US012629226B2

(12) United States Patent
Montagnani et al.

(10) Patent No.: US 12,629,226 B2
(45) Date of Patent: May 19, 2026

(54) MASTER CONTROLLER DEVICE COMPRISING A WEARABLE PORTION FOR ROBOTIC SURGICAL AND MICROSURGICAL TELEOPERATION, AND RELATED SYSTEM

(71) Applicant: MEDICAL MICROINSTRUMENTS, INC., Wilmington, DE (US)

(72) Inventors: Federico Montagnani, Pisa (IT); Nicola Pineschi, Pisa (IT); Emanuele Ruffaldi, Pisa (IT); Andrea Pratesi, Pisa (IT); Massimiliano Simi, Pisa (IT); Alexander Richard Joseph, Cambridge (GB); Andrew Duncan Pidgeon, Cambridge (GB); Samuel John Doyle, Cambridge (GB); Benjamin David Hopkins, Cambridge (GB); Niven Curtis-Woodcock, Cambridge (GB); Shadi Bavar, Cambridge (GB)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 39 days.

(21) Appl. No.: 18/443,135

(22) Filed: Feb. 15, 2024

(65) Prior Publication Data

US 2024/0277439 A1 Aug. 22, 2024

(51) Int. Cl.
*A61B 34/00* (2016.01)
*A61B 34/35* (2016.01)

(52) U.S. Cl.
CPC .............. *A61B 34/74* (2016.02); *A61B 34/35* (2016.02); *A61B 2034/741* (2016.02); *A61B 2560/0425* (2013.01)

(58) Field of Classification Search
CPC ........... A61B 2017/00425; A61B 2017/00438; A61B 2034/2051; A61B 2034/2055;
(Continued)

(56) References Cited

U.S. PATENT DOCUMENTS

| | | |
|---|---|---|
| 2006/0282063 A1 | 12/2006 | Gotani |
| 2018/0235719 A1 | 8/2018 | Jarc |
(Continued)

FOREIGN PATENT DOCUMENTS

| | | |
|---|---|---|
| WO | 2019099584 A1 | 5/2019 |
| WO | 2020188390 A1 | 9/2020 |
| WO | 2022175800 A1 | 8/2022 |

OTHER PUBLICATIONS

Italian Search Report received for Italian Serial No. IT202300002745 on Aug. 3, 2023, 7 pgs.

*Primary Examiner* — Wade Miles
*Assistant Examiner* — Zachary Joseph Wallace
(74) *Attorney, Agent, or Firm* — Merchant & Gould P.C.

(57) ABSTRACT

An unconstrained master controller device for a robotic system for medical or surgical teleoperation includes at least one wearable portion having a pair of wearable elements for the fingers of a surgeon and a control gripper for controlling at least one degree of freedom of a slave surgical instrument associable with the master controller device. The master controller device includes at least one internal degree of freedom of orientation which allows reorienting at least one wearable element of the pair.

21 Claims, 15 Drawing Sheets

(58) Field of Classification Search
CPC ...... A61B 2034/741; A61B 2560/0425; A61B
34/30; A61B 34/35; A61B 34/37; A61B
34/74
See application file for complete search history.

(56) References Cited

U.S. PATENT DOCUMENTS

| | | |
|---|---|---|
| 2019/0380791 A1 | 12/2019 | Fuerst |
| 2020/0197115 A1 | 6/2020 | Vakharia |
| 2020/0237467 A1 | 7/2020 | Savall |
| 2020/0390510 A1* | 12/2020 | Thompson ............. A61B 34/35 |

* cited by examiner (SLAVE)

ROLL SLAVE

PITCH SLAVE

YAW SLAVE

X SLAVE

Y SLAVE

Z SLAVE

OPEN/CLOSE

MASTER CONTROLLER DEVICE COMPRISING A WEARABLE PORTION FOR ROBOTIC SURGICAL AND MICROSURGICAL TELEOPERATION, AND RELATED SYSTEM

CROSS-REFERENCE TO RELATED APPLICATION

This application claims the benefit of priority to Application No. 102023000002745, filed Feb. 17, 2023 in Italy, and which application is incorporated herein by reference. To the extend appropriate, a claim of priority is made to the above-disclosed application.

FIELD OF THE INVENTION

The present invention relates to a master controller device.

The master controller device according to the invention is conceived for a robotic surgical teleoperation system.

The master controller device according to the invention is particularly suitable, although not uniquely intended, for use as a controller device of the type not mechanically constrained to the operative console.

The present invention further relates to a robotic system for surgical teleoperation comprising at least one master controller device.

PRIOR ART

Robotic surgery apparatuses are generally known in the art and typically comprise a central robotic tower or a cart and one or more robotic arms extending from the tower/cart. Each arm comprises a motorized positioning system (or manipulator) for moving a surgical instrument distally attachable thereto, in order to perform surgical procedures on a patient.

In order to control the robotic manipulator and thus the slave surgical instrument, the surgeon acts on one or more master controller devices, according to a master-slave teleoperation architecture.

In the known master devices, there are typically provided buttons to transmit control signals to the slave surgical instrument, and in particular where the surgical instrument is provided with a degree of freedom of opening/closing, i.e., gripping/cutting, the master device comprises an interface (for example formed by two cantilevered flaps) to actuate such a degree of freedom of opening/closing/gripping/cutting.

For example, document US-2018-0235719 shows a master controller device of the type constrained to the operative console, where the master controller device comprises a control gripper with two rigid flaps mounting respective wearable rings for receiving the surgeon's fingers.

In some prior art examples, the right and left master devices are each provided to be mounted to an attachment of the operative console and supported by a gimbal system.

Otherwise, master devices of the type mechanically/kinematically not constrained to the operative console ("groundless" or "unconstrained" according to the jargon adopted in this field) are known, i.e., of the "steering wheel" type, which is manipulated by the surgeon in a predeterminable three-dimensional tracking volume. Such unconstrained "steering wheel" master devices can be used for monolateral teleoperation without force feedback, for example.

Documents US-2020-0237467 and US-2019-0380791 show some examples of a controller device mechanically not constrained to the operative console, also referred to herein as a "User Interface Device" (UID), and in which, in particular, the master device comprises a wearable bracelet for receiving the surgeon's wrist.

Documents WO-2019-099584, US-2020-0197115 and US-2020-0390510 disclose some further examples of master devices of the unconstrained type, in particular in which rings are provided at the distal end of the rigid rods of the control gripper which are integrally fastened to the user's fingers for greater control.

Moreover, prior art document WO-2020-188390 shows a master controller device solution which is not constrained to the operative console, where a grippable handle is provided, which has on the top thereof a cantilevered attachment for the surgeon's thumb, forming a sort of joystick or control lever, and where such a joystick or control lever is perforated, i.e., it is a rigid ring for receiving the surgeon's thumb.

Unconstrained master devices are usually equipped with sensors, such as inertial platforms and/or position and/or orientation sensors, such as magnetometers and/or optical markers, to determine the command to be transmitted to the slave surgical instrument.

An example of a master device which is not constrained to the operative console is shown by document US-2006-0282063, where the master controller device is provided with a sensed glove wearable by the surgeon.

In some known examples, a magnetic field emitter is provided, which generates a tracking volume in which the position and orientation of two magnetometer-type sensors with six degrees of freedom provided on the body of the master device are tracked, so as to provide closing command signals to the slave device when the detected distance between the sensors is less than a certain threshold. For example, document WO-2022-175800 to the same Applicant shows an unconstrained master device solution in which the system control unit verifies the existence of predefined geometric relationships between two tracking sensors adapted to control the position, orientation and opening of a slave surgical device.

The known solutions of a master device not constrained to the operative console, although partially advantageous in some respects, are not at all without drawbacks.

In fact, the kinematics of the joints of the human hand can impose movements on the fingers which manipulate the unconstrained master device such as to transmit unwanted position coordinates to the slave device, or even worse can cause poor ergonomics during manipulation such as to cause a worse precision of movement, manipulation and control, a sense of insecurity of the user, until the master device falls from the hand, and the transmission of unwanted commands.

Therefore, the need is strongly felt to suggest a master device solution, particularly of the type not constrained to the operative console, which is of improved ergonomics with respect to known solutions, to allow an improved accuracy of master-slave teleoperation, avoiding or at least minimizing the problems of limited movement, poor manipulation and the risk of involuntary fall of the master device, while ensuring the surgeon to easily move the body of the master device between his/her fingers.

Solution

It is an object of the present invention to obviate the drawbacks complained of with reference to the prior art.

This and other objects are achieved by a device according to claim 1.

Some advantageous embodiments are the subject of the dependent claims.

According to an aspect of the invention, a master controller device for a robotic system for medical or surgical teleoperation comprises at least one wearable portion comprising a pair of wearable elements for a surgeon's fingers, and an operative portion for controlling at least one degree of freedom of a slave surgical instrument associable with the master controller device.

The operative portion preferably comprises a control gripper for controlling at least the slave degree of freedom of opening/closing of an associable slave device, such as a surgical gripper, a surgical scissor, a dilator, a needle driver/sutures cutter, and/or other surgical or microsurgical instruments.

The control gripper comprises one or more sensors or optical markers for determining on the basis thereof control signals to the slave device, while the wearable portion of the master device is preferably excluded from the control sensors to the slave device.

In accordance with a preferred embodiment, the control gripper comprises two rigid parts having at least one of the internal degree of freedom thereof therebetween. Said at least one internal degree of freedom of the control gripper is preferably a relative degree of motion towards/away from, such as a degree of freedom of opening/closing, for example, which is suitable for controlling an enslaved slave degree of freedom of opening/closing of the slave surgical instrument when operatively connected to the master controller device or another functionality of the slave device.

The wearable portion of the master controller device comprises at least one degree of freedom of orientation which allows at least one wearable element of said pair to be reoriented with respect to the control gripper.

In accordance with an embodiment, one wearable element is fixed on the control gripper and the other wearable element is mounted to be articulated to the control gripper, thereby achieving said at least one degree of freedom of orientation of the wearable portion. In other words, said at least one degree of freedom of orientation of the wearable portion can be achieved by a single joint between a wearable element and the control gripper.

Reorientation is preferably allowed in at least two directions, such as motion towards/away from the control gripper and rotation around the control gripper. The wearable element can be rigid, i.e., non-movable, and not be reorientable in one or more directions.

Said at least one degree of freedom can allow reorienting both wearable elements of said pair with respect to the control gripper.

Each wearable element of the pair can be reorientable with respect to the control gripper independently of the other wearable element, and for example each wearable element can be individually reorientable with respect to a respective rigid portion of the control gripper as well as with respect to a respective manipulation surface of the control gripper. In accordance with an embodiment, each wearable element is mounted to be articulated to the control gripper, and preferably is mounted to be articulated to a respective rigid part of the control gripper, where said at least one degree of freedom of orientation of the wearable portion is achieved by both joints.

In accordance with another embodiment, the wearable elements of the pair are fixed to each other, the wearable portion comprising them is rotatably mounted to the control gripper so as to achieve said at least one degree of freedom of orientation of the wearable portion. In such a case, said at least one degree of freedom is arranged between the wearable portion, for example comprising a pair of wearable elements, and the control gripper.

The provision of said at least one degree of freedom of the wearable portion prevents a movement of said at least one degree of freedom of the wearable portion from transmitting a command to the slave device, i.e., to the slave surgical instrument. Otherwise, the degree of freedom inside the sensed control gripper is conceived to control the slave device.

According to some embodiments, said at least one degree of freedom of the wearable portion is formed by one or more joints and/or articulated arms and/or by one or more elastically deformable (flexible) portions. For example, each wearable element is mounted on a joint and/or arm thereof of said one or more joints and/or arms.

Said at least one degree of freedom of the wearable portion preferably also allows repositioning the at least one wearable element of the pair with respect to the control gripper. For example, the repositioning of the wearable can result from the reorientation thereof with respect to the control gripper. For example, by maneuvering the wearable elements connected to respective arms with the fingers, a repositioning movement of the arms with respect to the control gripper, and in particular with respect to the respective rigid part of the control gripper, can be caused.

In accordance with an embodiment, the reorientation occurs around a definable roll axis extending substantially along the longitudinal extension direction of the control gripper and/or along the longitudinal extension direction of the respective rigid part. For example, the wearable portions are thus movable substantially circumferentially around the body of the control gripper. In accordance with an embodiment, the reorientation of the roll causes the circumferential rotation of the single wearable element with respect to the respective rigid part thereof of the control gripper. The two opposite manipulation surfaces intended to be manipulated by the fingers of a surgeon wearing the respective wearable elements can be convex and, even more preferably, convex and substantially cylindrical around the longitudinal axis in at least one closed configuration of the control gripper, to facilitate the roll movement between the control gripper and the wearable portion.

In accordance with an embodiment, the reorientation of the at least one wearable element is a reorientation in a direction of motion towards/away from the control gripper, it occurs around a definable axis transverse to the longitudinal extension direction of the control gripper, i.e., for example substantially in a direction parallel to the axis of a rotational joint arranged between the rigid parts of the control gripper itself and adapted to determine the internal degree of freedom of motion towards/away from or opening/closing of the sensed control gripper.

The at least one degree of freedom of the wearable portion can be achieved by a connection element, e.g., an arm, extending between a wearable element and the control gripper. Said connection element, for example an arm, can comprise one or more joints, for example of rotational or spherical type, and/or can comprise one or more elastically deformable portions.

Each wearable element preferably comprises a wearable ring, which can have a rigid annular body. In accordance with an embodiment, said wearable ring extends in a cantilevered manner from the respective arm, for example it projects outwards in a cantilevered manner, i.e., it is directed substantially radially externally with respect to a generally longitudinal axis of the control gripper. The arms can extend along the rigid parts of the control gripper and bring the rigid rings close to the manipulation surfaces provided on the outer side of the control gripper in a cantilevered manner.

The arm can comprise a rotational joint or a ball joint allowing each wearable element to be reoriented in three orthogonal directions with respect to the respective rigid part of the control gripper.

In accordance with an embodiment, the wearable portion of the master controller device comprises a pair of sterile clip armors, or sterile checks, which are snap-fitted to respective rigid parts of the control gripper, each clip armor of said pair comprising a wearable element of said pair, and preferably a respective arm as well. A sterile drape is typically interposed between each armor and the sensed control gripper. The armor is preferably configured to snap-fit to the body of the control gripper through said sterile drape, and to this end can comprise a fixing portion with a plurality of elastic teeth, which can be received in respective seats provided on the body of the two sensed rigid parts of the control gripper and which can have a rounded end so as not to damage the sterile drape.

The at least one degree of freedom of the wearable portion can be achieved by one or more elastic bodies, such as wire or sheet springs forming said arms. The one or more elastic bodies can comprise a pair of elastic arms each mounting a respective wearable element. The elastic arms of the pair are elastically flexible in the transverse direction with respect to the longitudinal axis of the control gripper, and for example in the circumferential direction therearound (roll) and/or towards/away therefrom.

The elastic arms are preferably preloaded towards a rest configuration spaced apart from the control gripper, i.e., in which the wearable elements are not in contact with the sensed control gripper, thus being cantilevered with respect to the control gripper even if substantially aligned therewith.

The at least one degree of freedom of the wearable portion can be achieved by one or more yielding laces or ropes which can be intertwined or woven.

The at least one degree of freedom of the wearable portion can comprise one or more degrees of freedom of orientation or roll and/or pitch and/or yaw. There can be provided degrees of freedom of translation, e.g., linear opening/closing, i.e., towards/away from along a linear trajectory, extension/retraction in a longitudinal direction, as well as buttons. For example, each arm of the pair provides roll, pitch, and yaw mobility to the respective wearable element. Limits can be placed on the three-dimensional mobility of the wearable element.

In accordance with an embodiment, the connection elements, for example joints and/or arms, provided between the control gripper and the wearable elements allow moving the wearable elements towards/away from, i.e., opening/closing, with respect to the control gripper.

By virtue of the suggested solutions, it is possible to expand the orientation workspace by manipulating or over-rotating the master controller device in hand in a safe and controlled manner.

In fact, the control gripper is sensed, i.e., it is configured to transmit control signals to the slave device, while the wearable portion has no sensors and therefore the manipulation thereof with respect to the control gripper is safe, and improves ergonomics for the surgeon. It is well understood that the sensors of the control gripper can be made as optical markers without circuitry.

The wearable portion can be made sterile and for example disposable, and can be associated with a sterile drape (by means of said armors or sterile coupling checks).

According to an aspect of the invention, a master controller device for a robotic surgical teleoperation system, comprises a wearable portion comprising at least one wearable element for at least one finger of a surgeon and an operative portion (e.g., a control gripper) for controlling at least one degree of freedom of a slave surgical instrument associable with the master controller device, said operative portion comprising one or more sensors for detecting position and/or orientation information of the master device, where the wearable portion comprises at least one connection element allowing the reorientation of said at least one wearable element with respect to the operative portion.

Said at least one connection element preferably comprises an arm, and the at least one wearable element preferably comprises a ring, said arm allowing the ring to be reoriented and/or repositioned with respect to the operative portion or control gripper. In accordance with an embodiment, said ring is reorientable with respect to said arm. Said arm can comprise a joint and/or an elastically deformable portion.

BRIEF DESCRIPTION OF THE DRAWINGS

Further features and advantages of the invention will become apparent from the following description of preferred embodiments, given by way of non-limiting indication, with reference to the accompanying drawings which are briefly described below. Note that references to "an" embodiment in this disclosure do not necessarily refer to the same embodiment, and are to be understood as at least one. Moreover, for reasons of conciseness and reduction of the total number of figures, a certain figure can be used to illustrate the features of more than one embodiment, and not all the elements of the figure can be necessary for a certain embodiment.

DETAILED DESCRIPTION OF THE INVENTION

Reference throughout this description to "an embodiment" means that a particular feature, structure or function described in relation to the embodiment is included in at least one embodiment of the present invention. Therefore, the formulation "in an embodiment" in various parts of this description do not necessarily all refer to the same embodiment. Moreover, particular features, structures or functions such as those shown in different drawings can be combined in any suitable manner in one or more embodiments.

In accordance with a general embodiment, there is provided a master controller device 110 (or master device 110) for a robotic surgical teleoperation system 100.

The robotic system 100 comprises at least one slave device 170 controllable by the master device 110.

Figure 1:
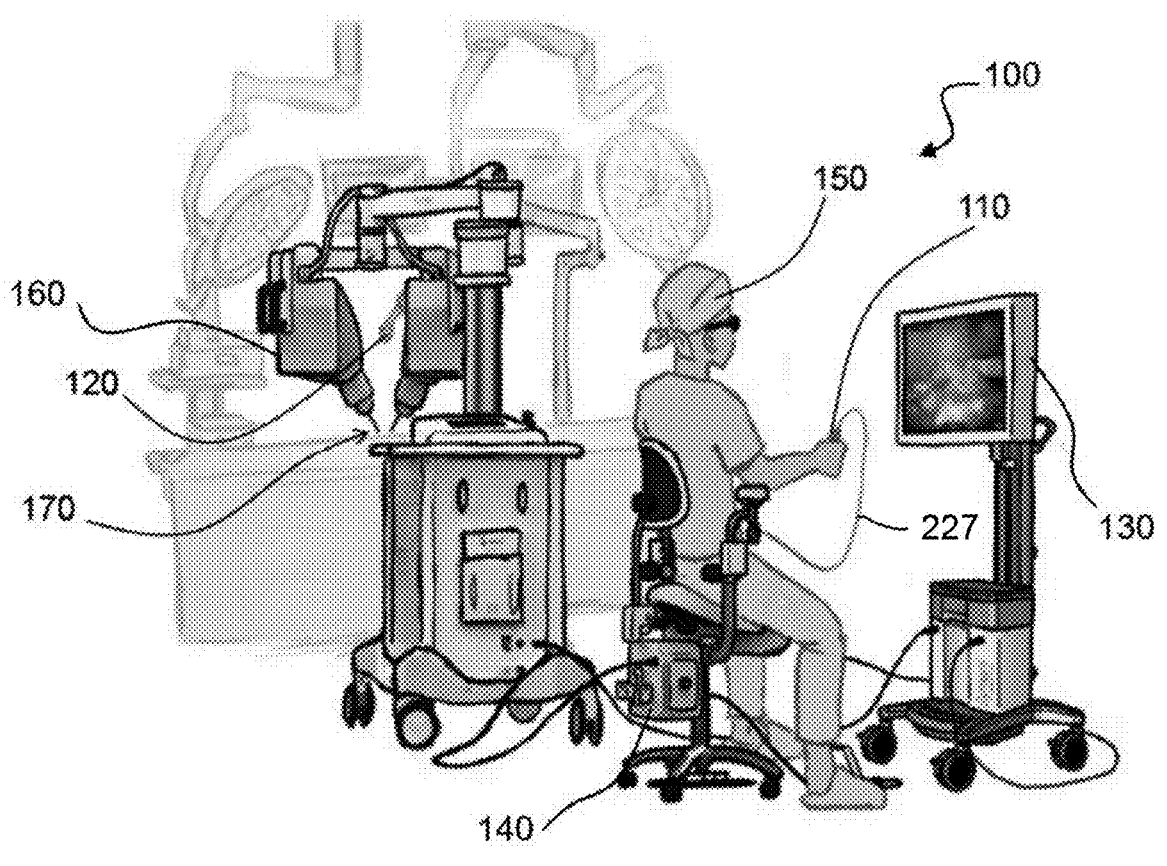
FIG. 1 shows in axonometric view a robotic system for medical or surgical teleoperation, according to an embodiment.

As shown for example in FIG. 1, the robotic system 100 can comprise a master console comprising a tracking system 140 for at least one master device 110 and a display 130 for displaying images acquired by a vision system 120, and a slave robotic assembly comprising at least one robotic manipulator 160 which moves a slave surgical instrument 170 under the control of the at least one master controller device 110.

Figure 2:
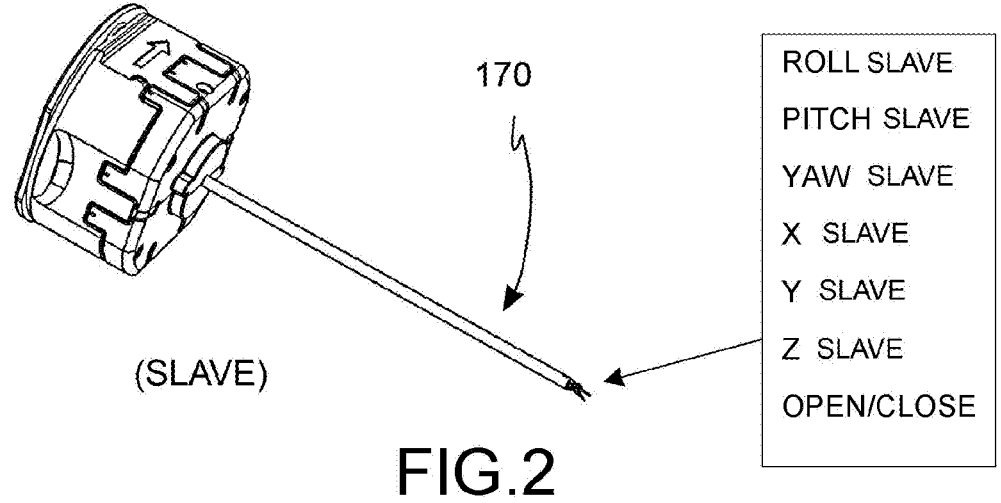
FIG. 2 shows in axonometric view a slave surgical instrument, according to an embodiment.

As shown for example in FIG. 2, the slave surgical instrument 170 can comprise a positioning shaft or rod having at the distal end thereof an articulated cuff provided with slave degrees of freedom of orientation (roll slave—pitch slave—yaw slave) and translation (X, Y, Z), as well as slave OPEN/CLOSE. The slave degrees of freedom of the slave surgical instrument 170 can refer to a definable virtual control point rigidly associated with the slave device and for example placed halfway between the tips or jaws movable in opening/closing of the slave surgical instrument.

It is understood that the teachings of this disclosure are applicable, mutatis mutandis, even if the master controller device 110 is intended for a surgical procedure simulation apparatus.

The master controller device 110 is preferably a master controller device of the type not constrained to an operative console 130, 140.

Advantageously, the master controller device comprises at least one wearable portion 210.

The provision of the wearable portion 210 allows the surgeon 150 to hold the master device securely in hand, avoiding or at least minimizing the risk of inadvertent dropping of the master device during a surgical teleoperation.

The wearable portion 210 comprises a pair of wearable elements 211, 212, intended to receive respective fingers F1, F2 of the hand of a surgeon 150. Preferably, each wearable element 211, 212 (e.g., wearable rings) of said pair receives a finger F1, F2 of the surgeon's hand (preferably thumb F2 and forefinger F1). More than two wearable elements can also be provided, for example for a total number of three or four wearable rings arranged in aligned and/or side by side and/or around a definable longitudinal axis of the master device.

The master controller device 110 further comprises an operative portion 220 which is configured to control at least one degree of freedom of a slave surgical instrument 170 associable with the master device. The operative portion 220 is sensed to control the slave device.

The operative portion 220 of the master device 110 is preferably a sensed control gripper 220 comprising two rigid parts 231, 232 relatively movable towards/away from each other OP/CL, and for example movable towards/away from each other in opening/closing OP/CL. In accordance with an embodiment, each rigid part of the control gripper is sensed, and for example comprises a sensor for acquiring information on six degrees of freedom of position and orientation of the rigid part on which it is mounted, so as to acquire redundant information on seven degrees of freedom of the control gripper, i.e., position, orientation and opening/closing (motion away from/towards).

For the purposes of this disclosure, the term control gripper 220 is used equivalently to operative portion 220, although it is understood that the operative portion can comprise, for example, radial control buttons to form the control gripper, without having a gripper-shaped body.

In accordance with a preferred embodiment, the control gripper 220 comprises two opposite manipulation surfaces 221, 222 intended to be manipulated by the fingers F1, F2 of a surgeon, which preferably face radially externally.

In accordance with a preferred embodiment, said operative portion 220 comprises one or more tracking sensors 223, 224 to detect at least some of the following: position, orientation, opening/closing OP/CL of the master device. The detection of said some of the position, orientation, opening/closing OP/CL of the master device is preferably carried out by the operative portion itself, i.e., the tracking sensors are secured to said operative portion 220. In accordance with a preferred embodiment, the master controller device 110 comprises two tracking sensors 223, 224, each at 6 degrees of freedom (three degrees of freedom of position, e.g., x, y, z, and three degrees of freedom of orientation, e.g., roll, pitch, yaw) for detecting position, orientation and opening/closing of the master device, as shown for example in FIG. 5. For example, each tracking sensor is secured to a rigid portion 231, 232 of the control gripper 220. The tracking sensors 223, 224 can comprise a pair of magnetometer-type sensors immersed in a tracking magnetic field when in operating conditions.

The sensors can comprise a cable connection 227 for data transmission and/or power to a control unit. The cable connection 227 can extend from the master device 110 for example towards the back of the surgeon's hand when in operating conditions.

The tracking sensors 223, 224 can comprise optical markers without circuitry.

The sensors for detecting at least some of position, orientation, opening/closing of the master device 110 are not necessarily tracking sensors, and can comprise: one or more inertial sensors in combination with a proximity sensor (for detecting the opening/closing OP/CL) and/or other suitable configurations of known sensors.

The master controller device 110 is preferably a master not mechanically constrained to the operative console.

The master controller device 110 is preferably a master of the wheel type for one-sided teleoperation, without force feedback.

With further advantage, the wearable portion 210 of the master controller device 110 comprises at least one degree of freedom which allows reorienting at least one wearable element 211, 212 of said pair with respect to the control gripper 220.

The reorientation preferably occurs along a direction Θ of motion towards/away from the control gripper 220 and/or along a roll direction ROLL around the control gripper 220.

Said at least one degree of freedom of the wearable portion can also allow repositioning at least one wearable element 211, 212 of said pair with respect to the control gripper 220. For example, the repositioning can result as an effect of reorientation.

Preferably, to reorient at least one wearable element 211, 212 of said pair with respect to the control gripper 220, one or more movement joints 217, 250 and/or one or more elastically deformable elements 215, 216 can be provided.

In accordance with a preferred embodiment, said at least one degree of freedom allows reorienting both wearable elements 211, 212 of said pair with respect to the control gripper 220. In other words, each wearable element 211, 212 of the pair can be reorientable with respect to the control gripper 220, thus achieving at least one degree of freedom of the wearable portion.

Said at least one degree of freedom is preferably achieved by a degree of freedom inside the at least one wearable portion 210 and the sensed control gripper 220 also comprises an internal degree of freedom thereof which allows relative motion towards/away from OP/CL, for example opening/closing OP/CL, between two sensed rigid parts 231, 232 of the control gripper 220.

By virtue of the provision of said at least one degree of freedom of the wearable portion, it is possible to reorient a wearable element 211, 212, and preferably both, with respect to the sensed control gripper 220.

Therefore, the arrangement of the wearable element 211, 212 does not transmit any command to the slave device 170 per sc.

It is thus possible to place the master device back in the surgeon's hand, for example by moving the fingers with respect to the sensed portions of the master device without risking either transmitting unwanted commands to the slave device or losing grip on the master device during teleoperation.

As mentioned above, the controller device 110 can be of the "steering wheel" type not constrained to the console 130, 140 and can control at least one degree of freedom of a slave surgical instrument 170 of a robotic surgical teleoperation system. To this end, in accordance with an embodiment, the master device 110 comprises a control gripper 220 which is monitored, sensed and capable of having the movement and/or orientation thereof transferred, from the robotic system 100, in movement and/or orientation of at least one slave degree of freedom, and a wearable portion 210 with at least one pair of wearable elements 211, 212 adapted to receive a portion of the surgeon's fingers. Therefore, when said master controller 110 is gripped during use, there is at least one relative degree of freedom of orientation between said control gripper 220 and said wearable portion 210 so that, while holding it in hand, the control gripper 220 can be manipulated and rotated between the fingers while the wearable portion 210 ensures the grip and movement thereof by means of a constraint with the user's fingers.

The control gripper 220 preferably consists of two rigid elements 231, 232 (rods) with at least one degree of freedom 230 (or articulated member, or joint) relative to and associated with the control of the opening/closing of said one slave surgical instrument 170. Such an articulated member 230 can be an elastic joint 230 or an elastic part (not shown) between said rigid elements 231, 232 of the control gripper 220. Said rigid elements 231, 232 of the operative portion 220 can be rods or tabs connected in such a relative joint 230. The rigid elements or parts 231, 232 can be rods extending along a direction which can coincide with the longitudinal direction X-X when in closing conditions of the control gripper 220, while the common rotation axis between the rods 231, 232 identified by the joint 230 is preferably directed orthogonally with respect to the common longitudinal extension axis X-X as well as the local extension axis of the rods 231, 232 themselves. The elasticity of the joint 230 is aimed at biasing the rigid parts 231, 232 being moved away towards a predeterminable opening configuration of the control gripper 220.

The wearable portion 210 can comprise two separate wearable half-portions 210' and 210" which together form the wearable portion 210. As shown for example in FIGS. 11-14 and 16, each wearable half-portion can comprise a wearable element 211 or 212 of the pair.

Figure 3:
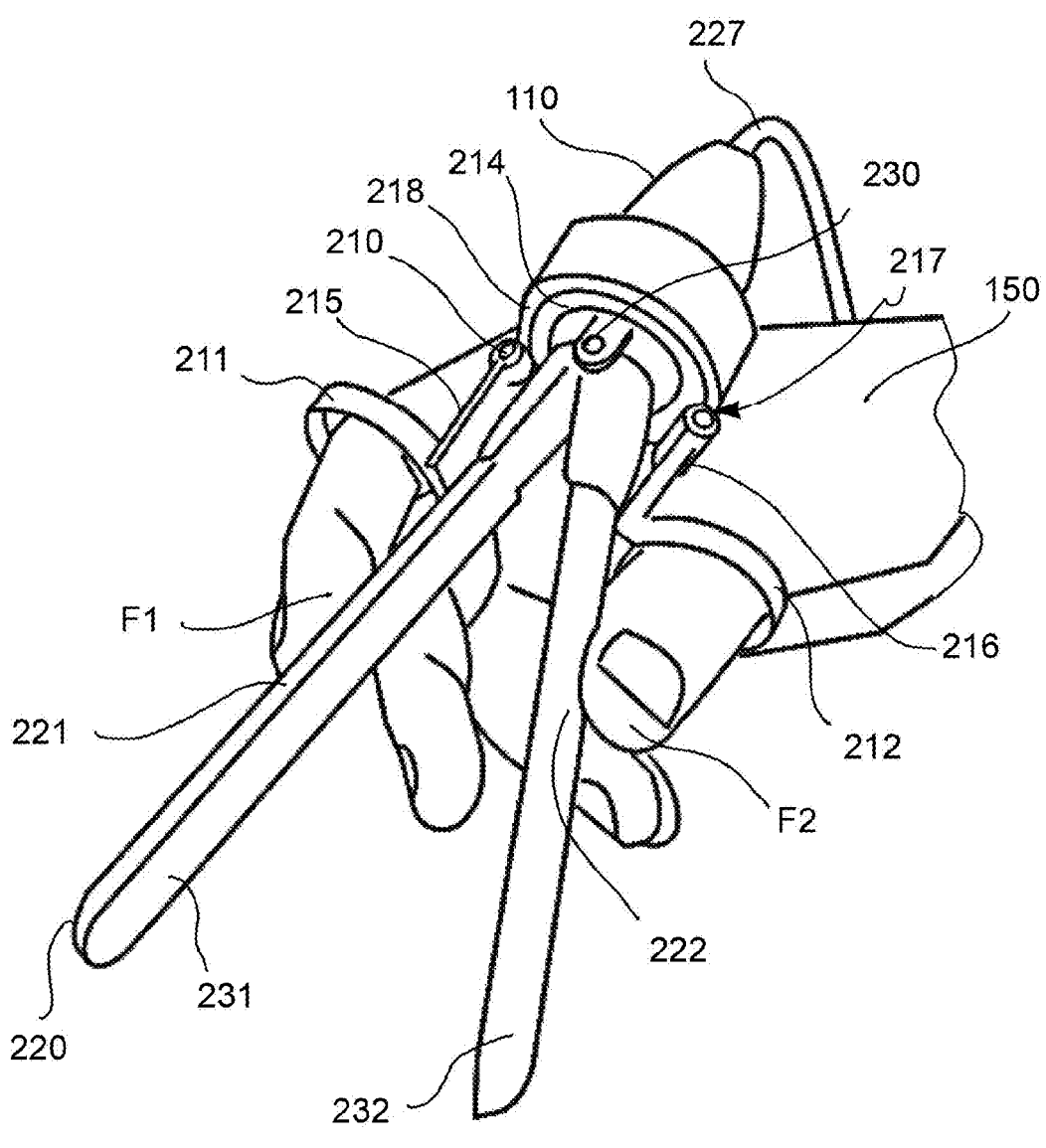
FIG. 3 shows in axonometric view a master controller device, according to an embodiment, held in hand by a surgeon.

As shown for example in FIG. 3, the wearable elements are preferably rings 211, 212 which can be intended to receive, respectively, thumb F2 and forefinger F1 of the surgeon's hand 150. The rings of the pair are preferably arranged opposite each other with respect to the securing body 214 or other body of the wearable portion 210, being arranged opposite with respect to the control gripper 220. The control gripper 220 preferably comprises two rigid parts 231, 232 and each ring 211, 212 of the pair is movable with respect to the control gripper due to the provision of a respective arm 215, 216 mounting at least one joint 217. For example, the rotation axis of the joint 217 can be substantially parallel to the rotation axis of the joint 230 between the rigid parts of the control gripper, allowing the wearable rings to be reoriented with respect to the control gripper in opening/closing. Each wearable ring can be secured to the distal end of the arm thereof, so that it projects radially outwardly, and can form a substantially 90° angle with the longitudinal extension direction of the arm, so that the fingers of the surgeon wearing the rings extend substantially along the respective arms. The provision of the transverse axis joint 217 can allow moving the ring away from the respective sensed rigid part, for example when the control gripper is in an open configuration with the spring of the joint 230 thereof at the end-of-stroke when in opening.

It is well understood that the term "rings" also means to indicate generally annular bodies for receiving the surgeon's fingers which are not necessarily shaped as closed rings and could also be open rings, for example open transversely, in such a case forming annular arcs 211, 212 for receiving the surgeon's fingers, although in accordance with a preferred embodiment the wearable elements 211, 212 are rings. Therefore, the wearable elements 211, 212 can be made as rings which are fitted onto the respective fingers F1, F2 and can be made as substantially rigid, open concave bodies.

As mentioned above, preferably, the operative portion 220 is configured to control at least the slave degree of opening/closing OPEN/CLOSE of a slave surgical instrument 170 associable with the master controller device 110, i.e., controllable by the master controller device 110 when in operating conditions. In such a case, the operative portion 220 can comprise at least one control gripper 220. The operative portion 220 or control gripper 220 can generally extend along a longitudinal direction X-X, at least when in a substantially closed configuration of the control gripper 220. For example, the longitudinal direction X-X can substantially coincide with a median axis between two rigid parts 231, 232 of the control gripper 220.

In accordance with a preferred embodiment, the master controller device 110 comprises an internal roll degree of freedom ROLL which allows the rotation of the wearable elements, for example rings, 211, 212 around the control gripper 220.

In other words, said at least one degree of freedom which allows the reorientation and repositioning of at least one wearable element with respect to the control gripper comprises a degree of freedom of roll around a definable roll axis which can be coincident with the longitudinal extension axis of the control gripper, substantially causing a rotation of the wearable elements in a generally circumferential direction with respect to the longitudinal extension of the control gripper and therearound. For example, the term degree of freedom of roll also means a local rotation of each wearable ring around a local roll axis coinciding with the longitudinal extension axis of each rigid part 231, 232 of the control gripper 220, i.e., a rotation of each wearable element 211 or 212 around the respective rigid part 231 or 232 thereof of the control gripper 220.

In accordance with an embodiment, between the wearable elements, for example rings, 211, 212 of the wearable portion 210 and the control gripper 220, the master device 110 comprises a pivotable roll joint 250 rotating around a common axis, which is directed substantially longitudinally i.e., along the longitudinal direction X-X, thereby achieving the internal degree of freedom of roll ROLL. The internal degree of freedom of roll can allow an angular movement along the roll direction about the common longitudinal axis between the wearable portion 210 and the control gripper 220 which is equal to or less than 90°, and preferably less than 90°. In accordance with an embodiment, said relative angular movement is less than or equal to 60°.

The rotation of the wearable elements, for example rings, 211, 212 can be conjoined around the common roll axis or can be independent of each ring 211 or 212 with respect to the other, for example, where the wearable elements, for example rings, are rigidly connected to each other i.e., are integral in roll rotation with each other. In this case, however, the wearable elements, for example rings, can be reorientable independently of each other, for example by providing joints 217 or articulated members 217 on the arms

215, 216, movable towards/away from each other Q (which can be substantially rigid in the roll direction ROLL). For example, where the wearable portion 210 is formed by two separate wearable half-portions 210', 210", the rotation of each ring 211, 212 is independent of the other.

The pivotable joint 250 between the wearable portion 210 and the control gripper 220 can be made by an internal degree of freedom of roll ROLL which is internal with respect to the wearable portion 210 of the master device. In other words, the pivotable joint 250 around the longitudinal axis X-X between the wearable portion 210 and the control gripper 220 of the master device 100 can be made by a degree of freedom of roll ROLL inside the wearable portion 210. The degree of freedom of roll ROLL, inside the wearable portion 210, can comprise rolling members and/or elastic bodies and/or laces, for example intertwined or woven.

In accordance with an embodiment, as mentioned above, the wearable portion 210 is pivotally connected to the control gripper 220 of the master controller device, so that the control gripper can be rolled ROLL around a longitudinal axis X-X with respect to the wearable portion, making the pivotable joint 250. The pivotable joint 250 is preferably made as a coaxial pivotable joint.

As mentioned above, by virtue of such a master device 110, the control gripper 220 or operative portion 220 can be reoriented with respect to the wearable elements, for example rings, 211, 212 while remaining constrained to the hand or to some fingers by said wearable portion 210. The wearable elements, for example rings, can be repositioned with respect to the control gripper or operative portion without transmitting any command to the slave device.

Figure 4:
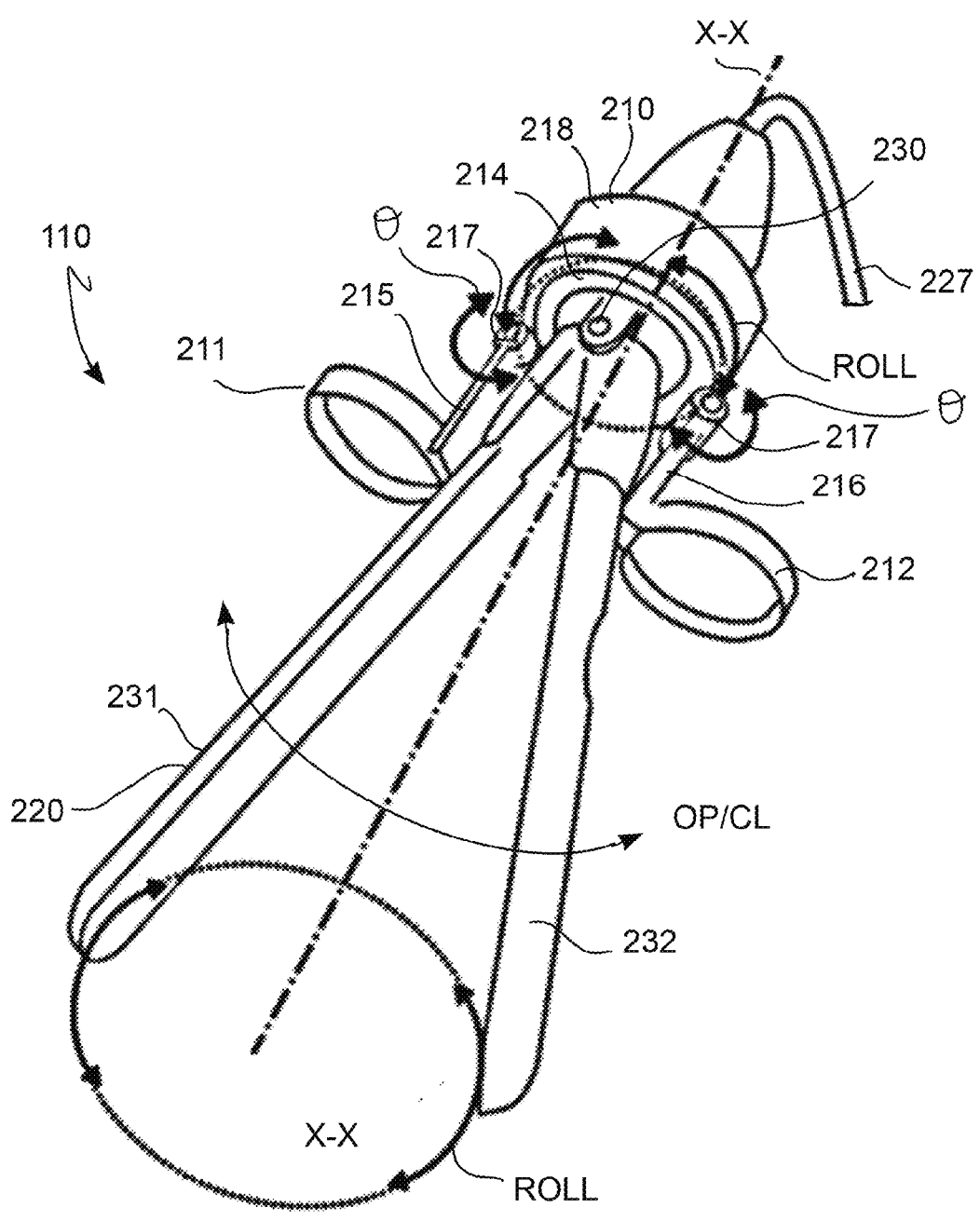
FIG. 4 shows in axonometric view the master device of FIG. 3.

In particular, by virtue of such a master device 110, as shown for example in FIG. 4, the control gripper can be rolled with respect to the wearable elements, for example rings, 211, 212 of the wearable portion 210, and in particular the wearable elements, for example rings, rotate together with roll with respect to the control gripper, while a further degree of freedom of rotation Θ around a transverse axis, i.e., rotation away from/towards, is provided by virtue of the joint 217 (hinge) mounted on each arm 215, 216 of the pair of arms provided at the end thereof with the respective wearable elements, for example rings.

The provision of wearable elements, for example wearable rings 211, 212, allows keeping the master device 110 firmly in the hand of the surgeon 150 even during such operations of different orientation of the control gripper 220 and in particular the roll thereof. Rolling the operative portion 220 between the fingers F1, F2 is an operation which can be desirable for the surgeon 150 during teleoperated surgery to relieve the nerve tension thereof as well as to appropriately maneuver the slave surgical instrument 170. By virtue of the suggested solutions, it is possible to secure, by means of the wearable elements, for example rings, the master device 110 firmly to the same fingers F1, F2 of the surgeon which maneuver the control gripper 220 also in roll ROLL around a longitudinal axis X-X.

In accordance with a preferred embodiment, the pivotable roll joint 250 between the wearable portion 210 and the control gripper 220 is a reversible or removable connection, i.e., the wearable portion 210 and the control gripper 220 can be mounted and disassembled, if necessary, for example to interpose a sterile drape 240 therebetween and/or to mutually reposition them. There can be provided a securing body 214 connected to both wearable elements, e.g., rings, 211, 212, preferably by respective arms 215, 216, where the fixing body 214 is preferably annular and is fitted onto the control gripper 220, e.g., close to the joint 230 between the sensed rigid parts 231, 232. In accordance with a preferred embodiment, the pivotable roll joint 250 is a coaxial pivotable joint and comprises one or more rolling members, such as ball bearings. The rolling members are not necessarily interposed between the wearable portion 210 and the control gripper 220, and for example the wearable portion 210 can comprise a portion or body 214 secured to the control gripper and a movable portion 218, for example a movable mounting ring 218 fitted onto the fixed portion 214, in which the wearable elements, for example rings, 211, 212 rotate around the body 214 with interposition of rolling members between the wearable elements, for example rings, 211, 212 and the fixed body 214 (between the movable ring 218 and the fixed body 214). In other words, the wearable elements, e.g., rings, 211, 212 for the surgeon's fingers F1, F2 can be mounted to a movable ring 218 which is rotatably mounted to the fixed portion 214 secured to the control gripper 220 of the master device 110.

In accordance with an embodiment, the roll movement ROLL allowed to the wearable elements, e.g., rings, is synchronous i.e., integral in rotation and/or occurs perfectly along a circular trajectory around the longitudinal axis X-X. In this case the arms 215, 216 are preferably rigid and the internal degree of freedom of roll is achieved with rolling members.

Figure 9:
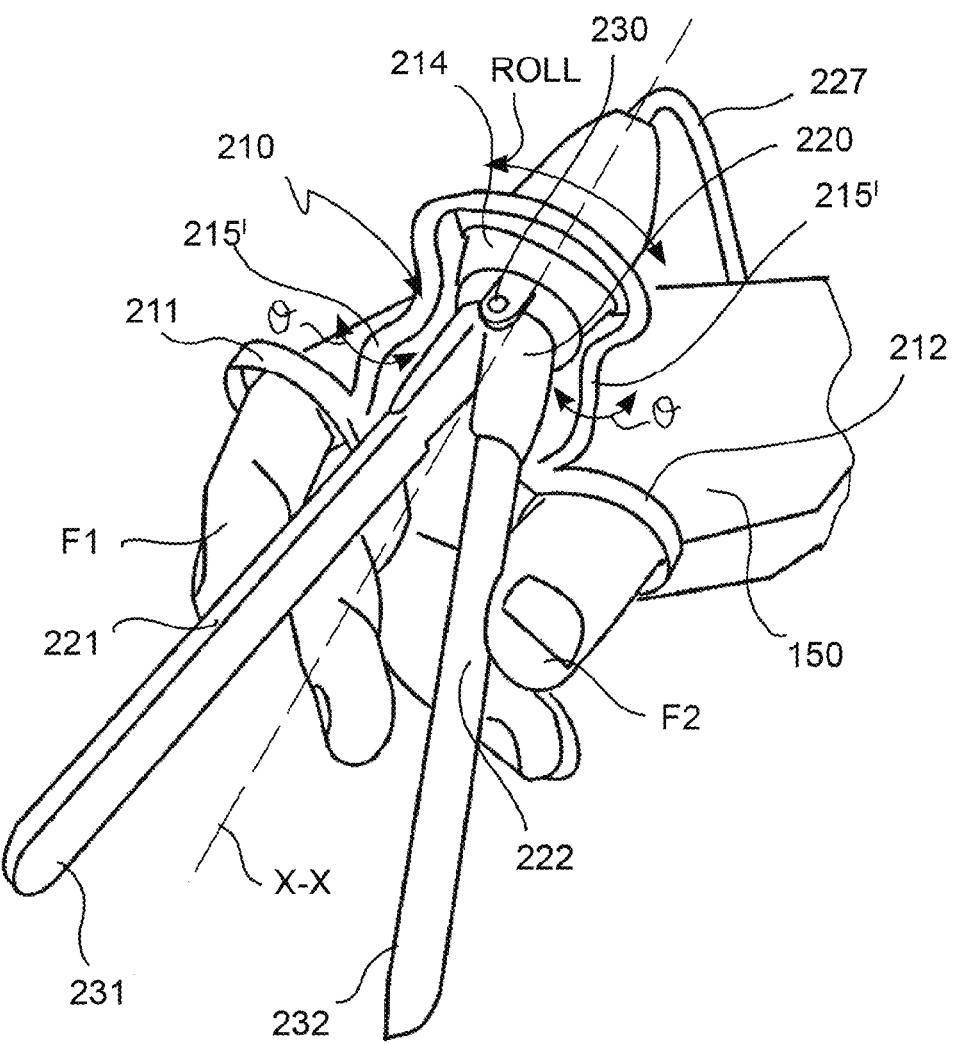
FIG. 9 shows in axonometric view a master controller device, according to an embodiment, held in hand by a surgeon.

As shown for example in FIG. 9, the pivotable roll joint between the wearable portion 210 and the control gripper 220 can comprise one or more elastic connection elements 215, 216, or clastic arms 215, 216, which are made elastically flexible in the roll rotation direction ROLL. Alternatively or additionally, said elastic bodies or clastic arms 215, 216 can be flexible in the direction of opening/closing i.e., of motion towards/away from @ the control gripper, thereby forming said at least one degree of freedom of the wearable portion. Said elastic bodies can be made as wire springs and/or foil springs, for example, by providing a folded elongated element. Said yielding elastic bodies can be made of a polymer material, for example high molecular weight polyethylene (UHMWPE), rubber, silicone.

Therefore, in accordance with an embodiment, the provision of the elastic elements forms the internal degree of freedom of roll ROLL, i.e., substantially circumferential rotation with respect to the longitudinal axis of the control gripper 220, although not necessarily the movement allowed to the wearable elements, for example rings, must be synchronous and/or must occur perfectly along a circular trajectory around the longitudinal axis X-X. Moreover, the provision of said elastic arms 215, 216 allows moving (reorienting) relatively away from/towards Θ the wearable elements, for example wearable rings, as well as allows moving (reorienting) away from/towards Θ an individually wearable ring 211 or 212 with respect to the respective rigid part 231 or 232 of the control gripper 220, as well as with respect to the respective manipulation surface 221 or 222 facing thereto.

As mentioned above, in accordance with a preferred embodiment, the wearable portion 210 comprises a pair of connection elements 215, 216, such as arms 215, 216, each mounting a respective wearable element 211, 212 of said pair. The arms 215, 216 can be clastic arms or elastic joints which achieve the degree of freedom of roll ROLL. The arms 215, 216 can be elastic arms which achieve the degree of freedom of motion towards/away from Θ of the wearable elements with respect to the control gripper. Said arms 215, 216 can be made in the form of yielding laces movable with respect to the control gripper 220.

In accordance with an embodiment, a first arm 215 and a second arm 216 are provided, each of which mounts a respective wearable element 211 or 212 of the pair, where, preferably, the wearable elements are mounted in a cantilevered manner at the end of the respective arm 215, 216. Preferably, the wearable elements are rings 211, 212 projecting in a cantilevered manner in the direction of opening i.e., away from the common longitudinal axis X-X. In other words, the wearable elements, for example rings, 212, 213 of said pair preferably have a rigid body extending in a cantilevered manner in an external transverse direction. The rings thus extend in a cantilevered manner from the respective arms away from (opening) the respective rigid part 231, 232 of the control gripper 220 as well as from the respective manipulation surface 221, 222.

Each arm 215, 216 can comprise a joint 217, for example a rotational joint 217, along the extension thereof to allow a movement in the direction towards/away from Θ of the wearable element with respect to the control gripper, or in other words in the internal/external transversal direction, which is transversal or radial with respect to the longitudinal direction. As mentioned above, said two opposite arms can be elastic, and each of them mount a ring of said pair of rings provided in a cantilevered manner at an end thereof. The rings of said pair are for example rings having a rigid annular edge.

The arms 215, 216 can extend substantially in the longitudinal direction X-X from the wearable portion 210 which is constrained to the control gripper 220, such as from the movable portion 218 or the fixed body 214 or by means of said sterile coupling checks 241, 242, for example. Preferably the arms 215, 216 extend along the respective rigid portions 231, 232 of the control gripper 220.

In accordance with an embodiment, the first wearable portion 210, and preferably the fixed body 214, secured to the operative portion 220, comprises a through hollow body in the longitudinal direction X-X (for example a fixed mounting ring 214), which is fitted onto the second operative portion 220. Preferably, the hollow body is secured, for example interlocked and/or snap-fitted, to the second operative portion, and can comprise said internal degree of freedom of roll. The provision of said hollow body can allow, when assembling the wearable portion 210 to the operative portion 220, fitting the wearable portion 210 onto the operative portion, for example in the longitudinal direction X-X. For example, the wearable portion 210 can be fitted onto the operative portion 220 after at least partially reclosing the degree of freedom of opening/closing OP/CL of the control gripper of the operative portion 220, to allow the body of the control gripper 220 to cross the cavity of the securing body 214 longitudinally.

In accordance with an embodiment, the rings of the pair of rings are mounted so as to be integral with each other in roll rotation ROLL around the longitudinal axis X-X, i.e., around the operative portion 220 of the master controller device 110. In other words, the rings preferably roll in coordination with each other, always being positioned substantially opposite each other with respect to the body of the operative portion 220, when in operating conditions, while ensuring the internal degree of freedom of roll ROLL of the master device 110. To this end, there can be provided said movable mounting ring 218 associated with the fixed portion 214 secured to the operative portion 220.

In accordance with an embodiment, the master device comprises a sterile drape 240 covering the operative portion 220 which is secured to the operative portion 220 by means of the wearable portion 210. To this end, said fixed mounting ring 214 can be provided. In accordance with an embodiment, the sterile drape 240 is interposed between the operative portion and the wearable portion, and preferably between the hollow body of the wearable portion 210 and the operative portion 220.

In accordance with a preferred embodiment, two opposite covering elements 241, 242 (e.g., sterile clip armors or sterile checks 241, 242) are mounted on the control gripper 220, which are fixed to the control gripper 220 through the body of the sterile drape 240 to form the manipulation interface for the surgeon's fingers F1, F2. In other words, each sterile clip armor 241, 242 can mount a wearable element 211, 212 so that the two sterile clip armors are mounted to the rigid parts of the control gripper forming the manipulation interfaces.

In accordance with an embodiment, the fixed hollow body 214 of the wearable portion 210 is made of two separate half-bodies 214a, 214b each provided with one of said two wearable elements, for example rings, 211, 212. Preferably, said two separate half-bodies mount a movable portion 218 or movable ring 218, for example by interlocking and/or snap-fitting.

As mentioned above, in accordance with a preferred embodiment, the second operative portion 220, for example a control gripper 220, comprises two opposite manipulation surfaces 221, 222 intended to be manipulated by a surgeon's fingers F1, F2. Preferably, the two opposite manipulation surfaces 221, 222 are convex. In accordance with a preferred embodiment, said two opposite manipulation surfaces 221, 222 are convex circumferentially around the longitudinal axis and are also substantially cylindrical with respect to the same longitudinal axis X-X. It is thus possible to promote the rolling of the operative portion between the surgeon's fingers, utilizing the internal degree of freedom of ROLL of the wearable portion 210, where provided, when the control gripper is in the closed position.

The two opposite manipulation surfaces 221, 222 of the operative portion are preferably movable with each other in opening/closing OP/CL to command the slave degree of freedom of opening/closing OPEN/CLOSE of the slave device 170. To this end, the sensors can be mounted integrally therewith. As mentioned above, in accordance with an embodiment, the second operative portion 220 comprises one or more sensors to determine at least one of the following: position of the master device, orientation of the master device, degree of opening/closing OP/CL of the master device. The tracking sensors 223, 224 can be integral in opening/closing with the manipulation surfaces 221, 222 of the operative portion 220 of the master device.

In accordance with an embodiment, the control gripper has two rigid parts 231, 232 each provided with a manipulation surface 221, 222 thereof, said two rigid parts being constrained in a joint 230 to rotate around a common axis, where, preferably, the joint is elastically preloaded in an opening configuration.

In accordance with a preferred embodiment, the internal degree of freedom of the master device 110, allowing the rotation of the wearable elements, for example rings, 211, 212 with respect to the manipulation surfaces 221, 222 of the control gripper, avoids transmitting commands to the slave device per se. In fact, the tracking sensors are provided only on the operative portion 220, i.e., on the control gripper 220, as mentioned above.

Each ring 211 or 212 of the first wearable portion can be made orientable independently of the other ring 212 or 211. For example, one or more joints 217 are provided between the wearable elements, e.g., rings, 211, 212 of the wearable portion 210. At least one joint can be provided between the movable body 218 and each respective ring 211, 212, for example along the longitudinal extension of a respective arm 215, 216.

As shown for example in FIG. 4, the wearable elements 211, 212 can be two wearable rings articulated to the body 214 by means of rotational joints 217 placed on the respective arms 215, 216.

Figure 5:
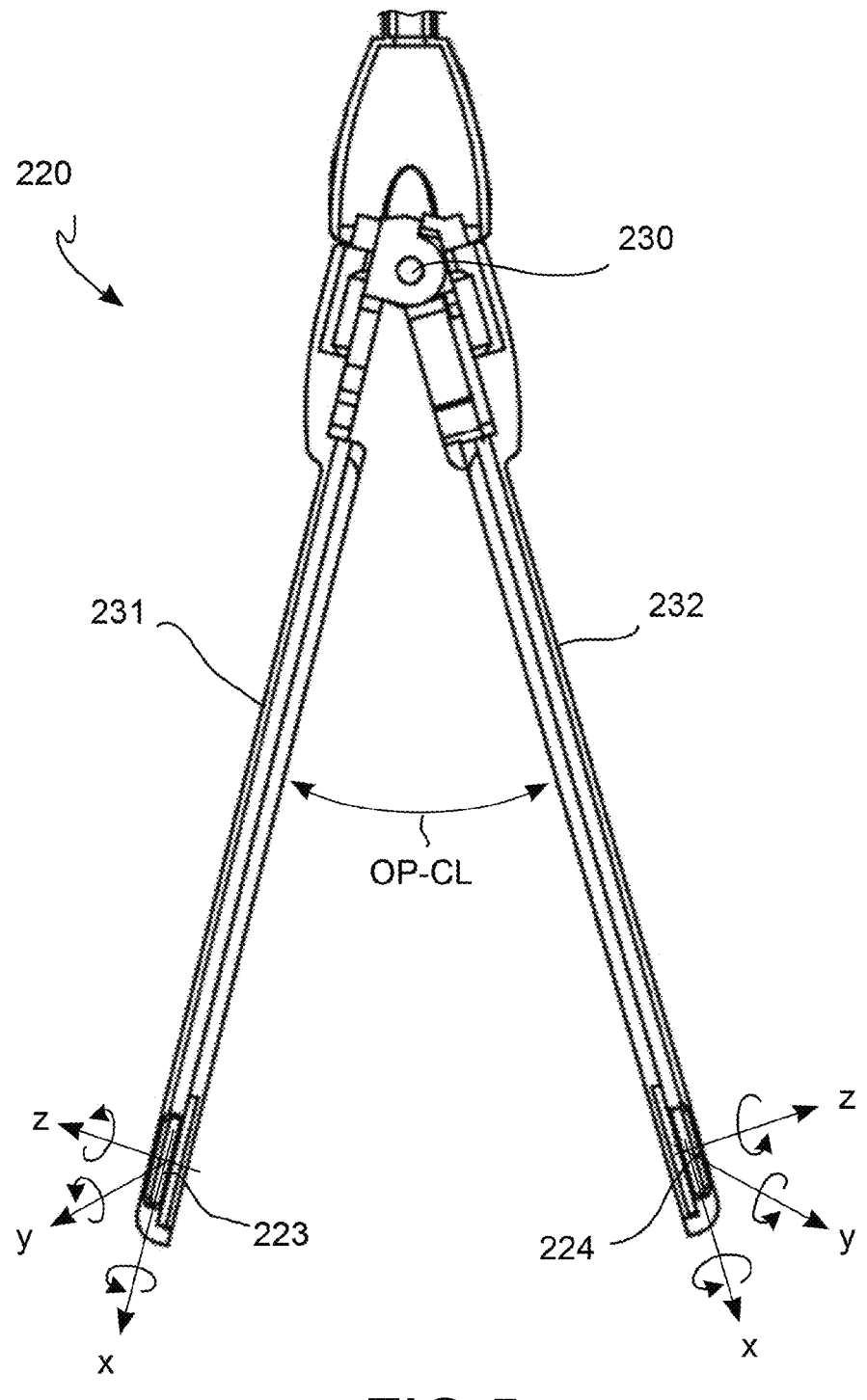
FIG. 5 shows the control gripper of the master controller device of FIG. 3 in vertical elevation.

As shown for example in FIG. 5, the control gripper 220 can comprise two rigid parts 231, 232 each associated with a respective tracking sensor 223, 224 at six degrees of freedom (position and orientation), where a rotational joint 230 is provided between the rigid parts, and where each rigid part of the control gripper comprises a manipulation surface 221, 222 thereof close to or at the respective wearable ring 211, 212.

Figure 6:
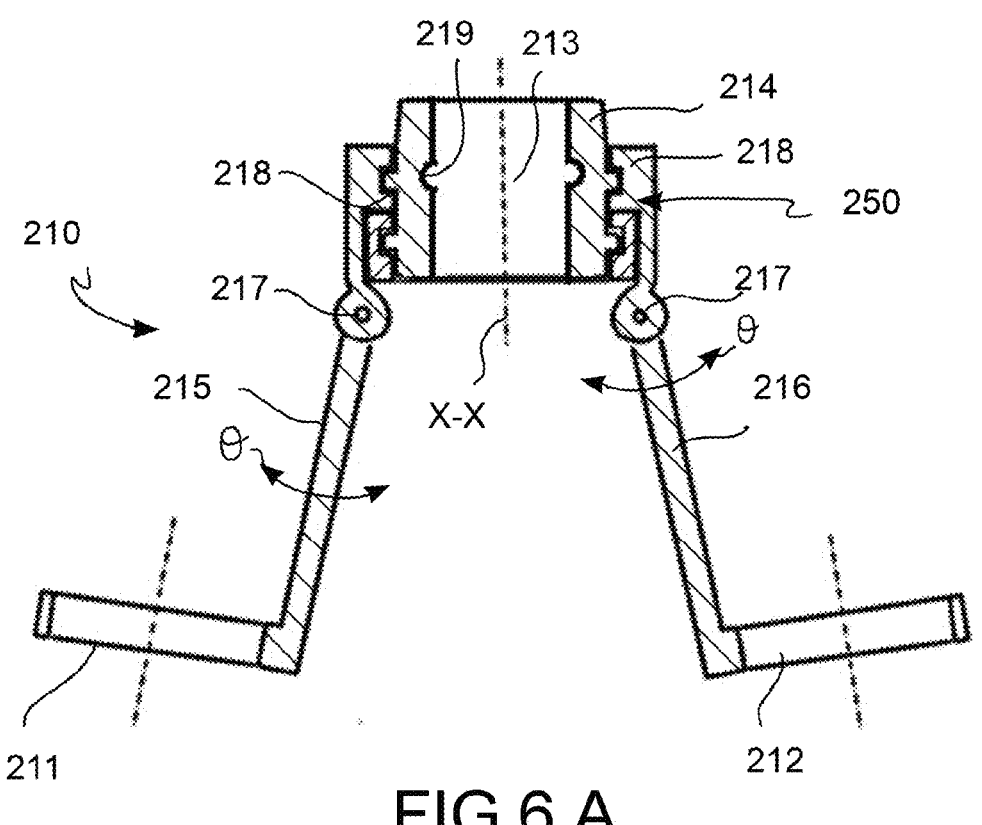
FIG. 6A shows in section the wearable portion of the master controller device, according to an embodiment.
FIG. 6B shows in axonometric view a master controller device, according to an embodiment, comprising the wearable portion of FIG. 6A.
Figure 6:
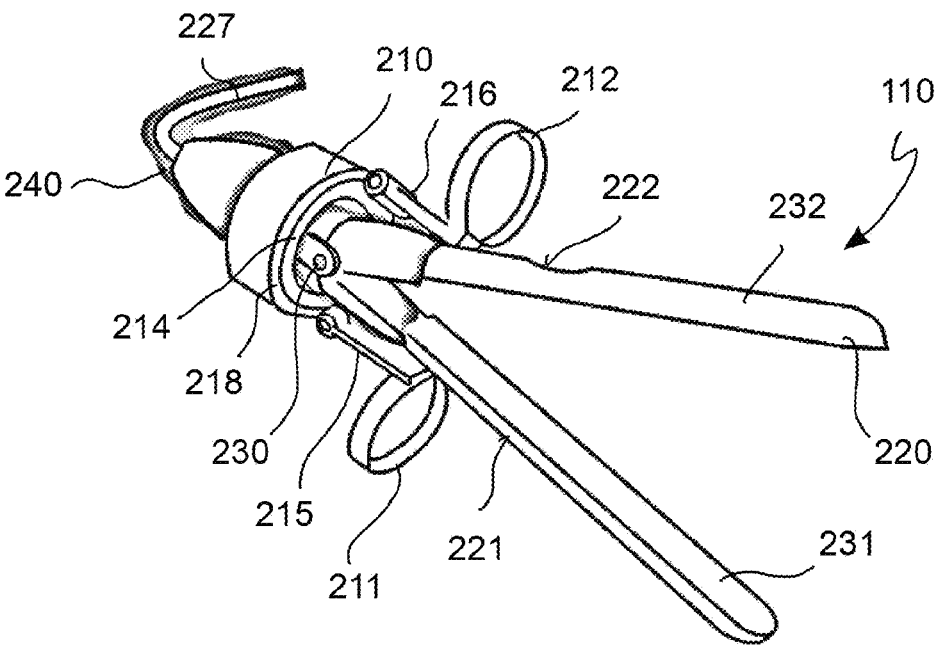

As shown for example in FIGS. 6-A and 6-B, the wearable portion 210 can be fitted onto a sterile drape 240 covering the operative portion 220.

Figure 7:
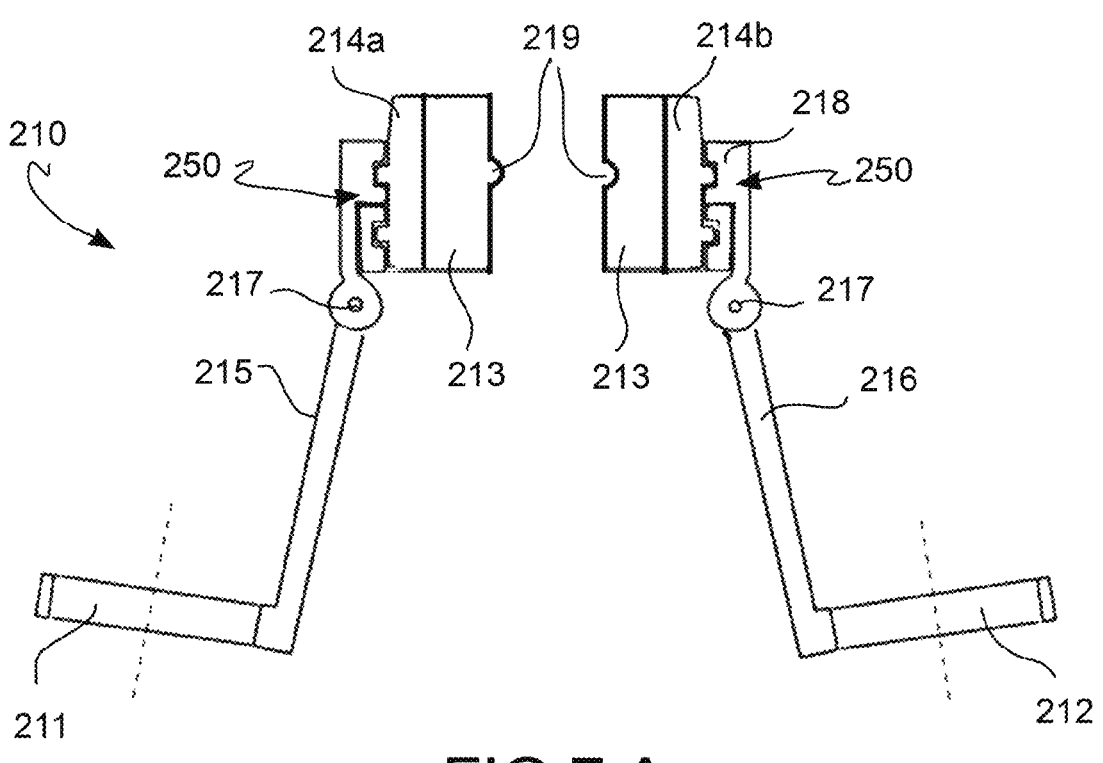
FIG. 7A shows in section and in separate parts a wearable portion of a master controller device, according to an embodiment.
FIG. 7B shows in axonometric view a master controller device, according to an embodiment, comprising the wearable portion of FIG. 7A.
Figure 7:
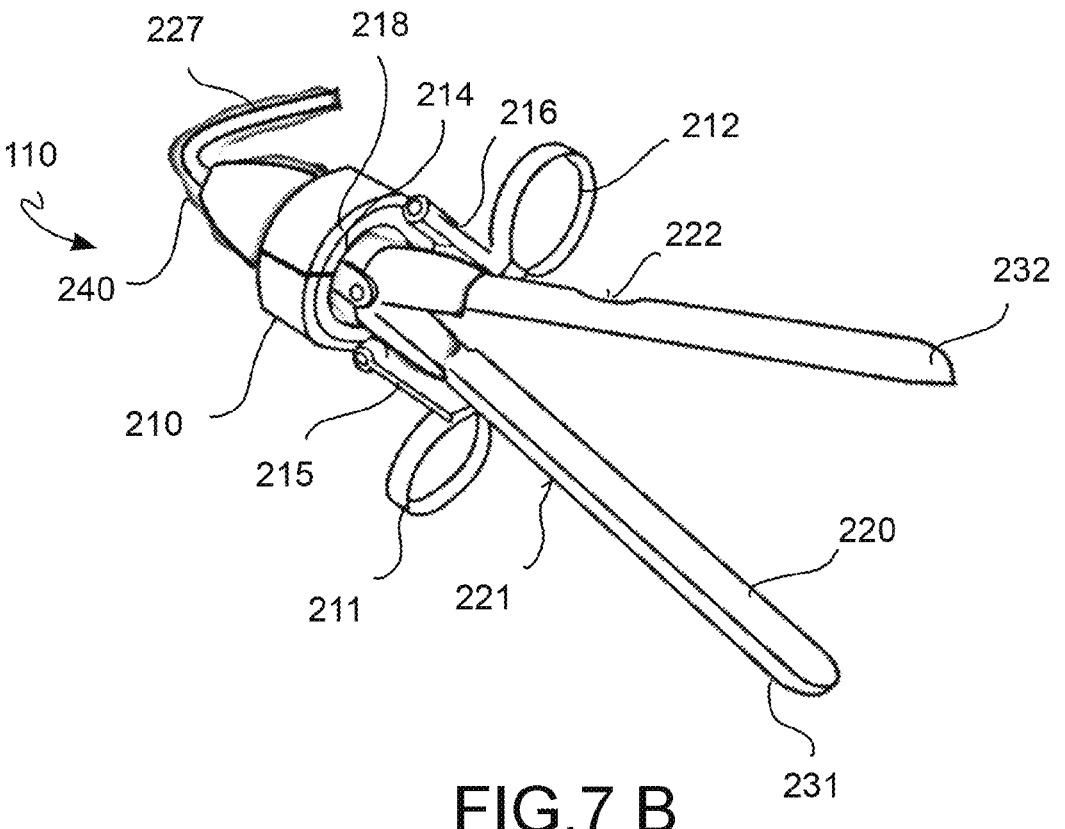

As shown for example in FIGS. 7-A and 7-B, the wearable portion 210 can be formed by two half-bodies 214-a, 214-b, and in particular two half-bodies which jointly form the fixed hollow body 214 fitted onto the operative portion 220, said two half-bodies being assembled on the sterile drape 240 to cover the operative portion 220.

Figure 8:
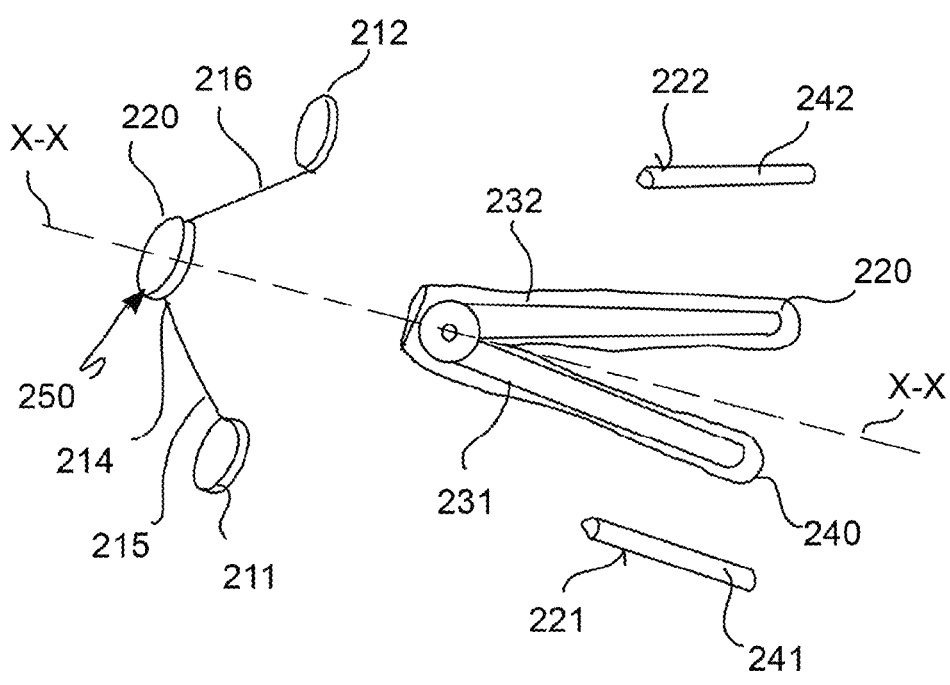
FIG. 8A shows in axonometric view and in separate parts a master controller device, according to an embodiment.
FIG. 8B shows in axonometric view and in separate parts a master controller device, according to an embodiment.
Figure 8:
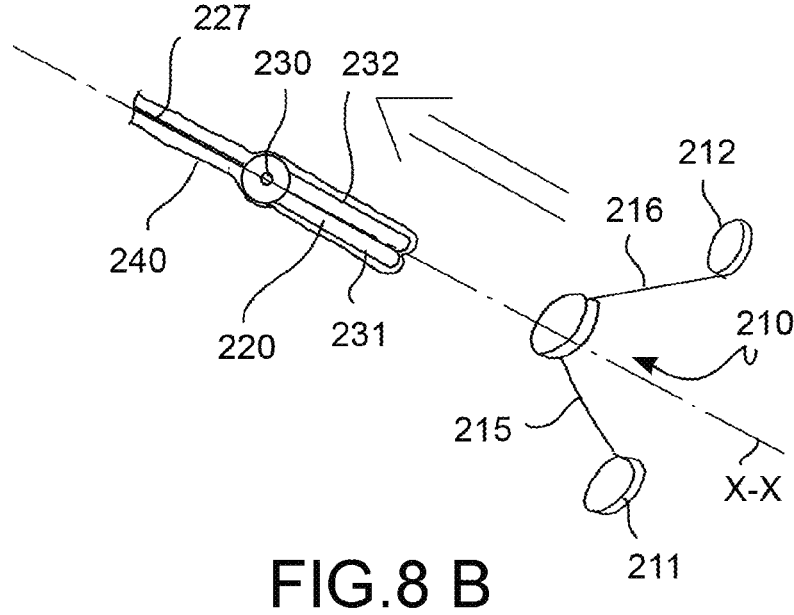

As shown for example in FIG. 8-A, sterile accessories 241, 242 or cheeks 241, 242 can be provided, which for example couple through the sterile drape 240 to respective rigid parts 231, 232 of the control gripper 220, to manipulate the master device 110 in a sterile environment. Such sterile accessories 241, 242 can form with the back thereof the manipulation surfaces 221, 222 of the operative portion.

As shown for example in FIG. 8-B, the assembly of the wearable portion 210 to the operative portion 220, can occur according to the following steps: closing the control gripper 220, bringing the manipulation surfaces 221, 222 towards each other; (ii) fitting the hollow body 214 of the wearable portion 210 on the operative portion 220 from the part of the operative portion comprising the free ends of the respective rigid parts.

Figure 10:
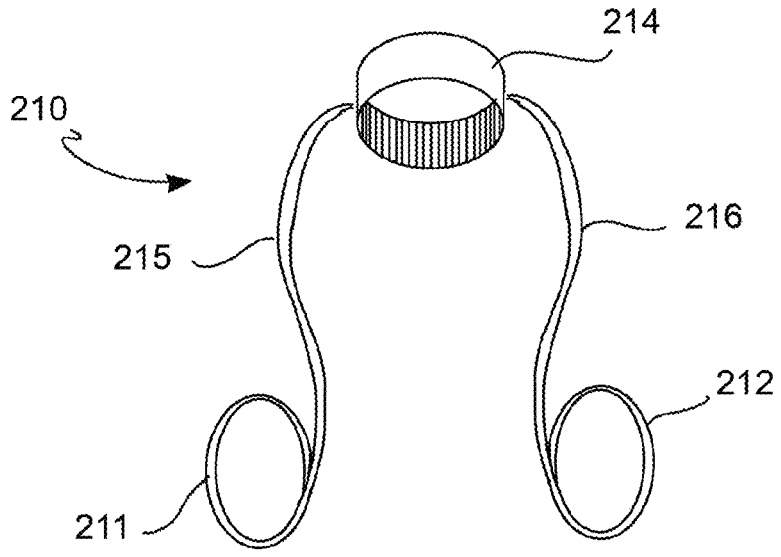
FIG. 10A shows in axonometric view a wearable portion of a master controller device, according to an embodiment.
FIG. 10B shows in axonometric view a master controller device, according to an embodiment, comprising the wearable portion of FIG. 10A.
Figure 10:
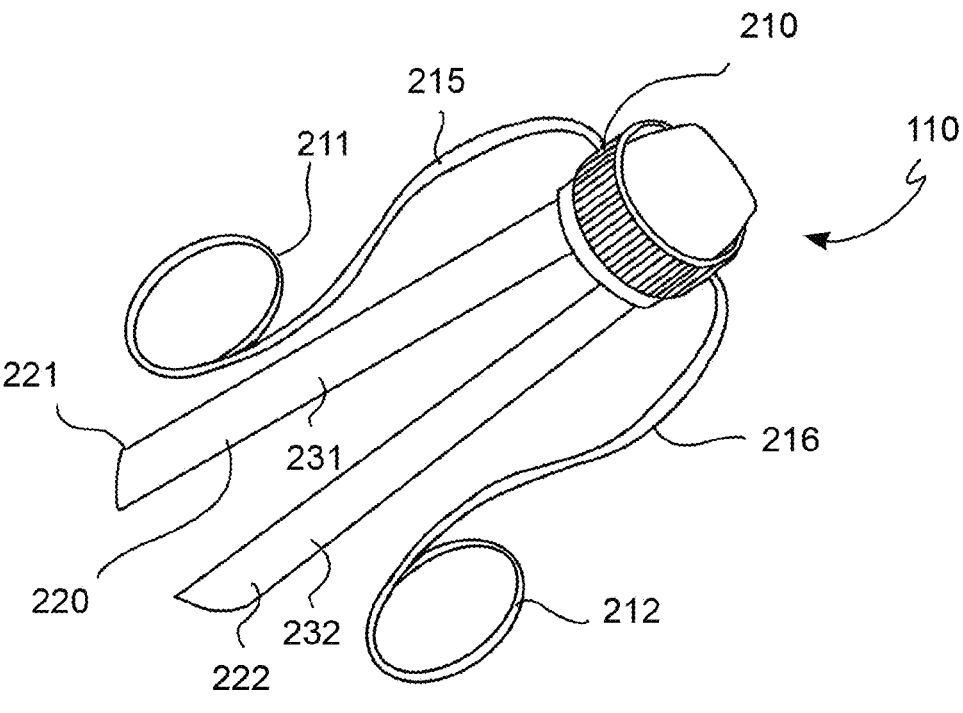

As shown for example in FIGS. 10-A and 10-B, the arms 215, 216 of the wearable portion can be laces, preferably elastic laces.

Figure 11:
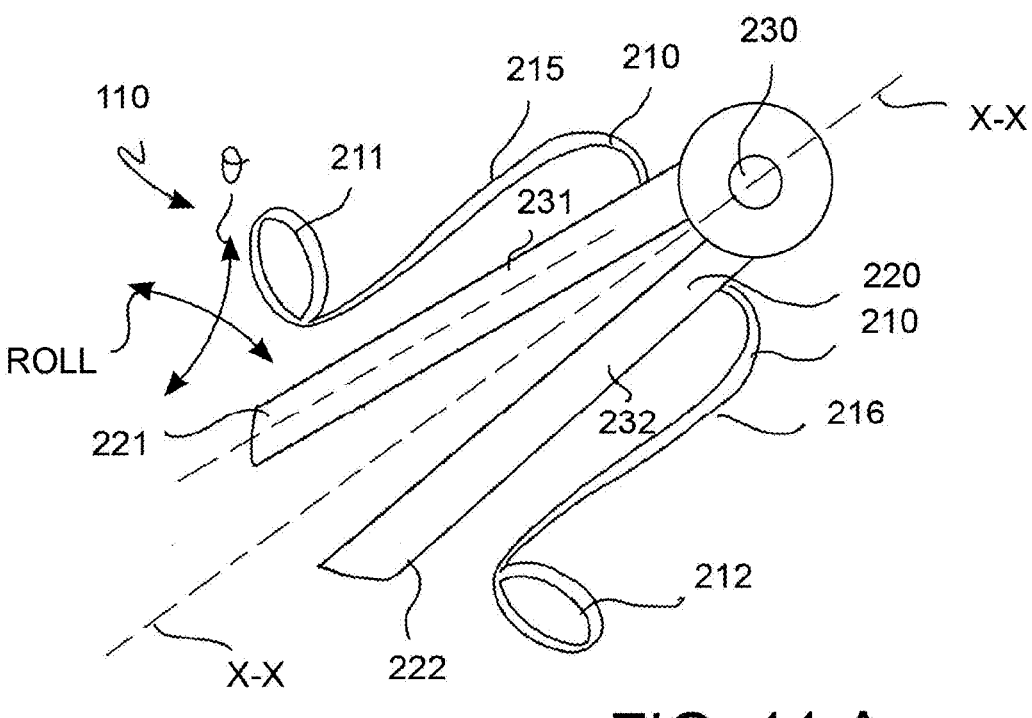
FIG. 11A shows in axonometric view a master controller device, according to an embodiment.
FIGS. 11B and 11C diagrammatically show some possible degrees of freedom of orientation of the wearable portion of the master device of FIG. 11A.
Figure 11:
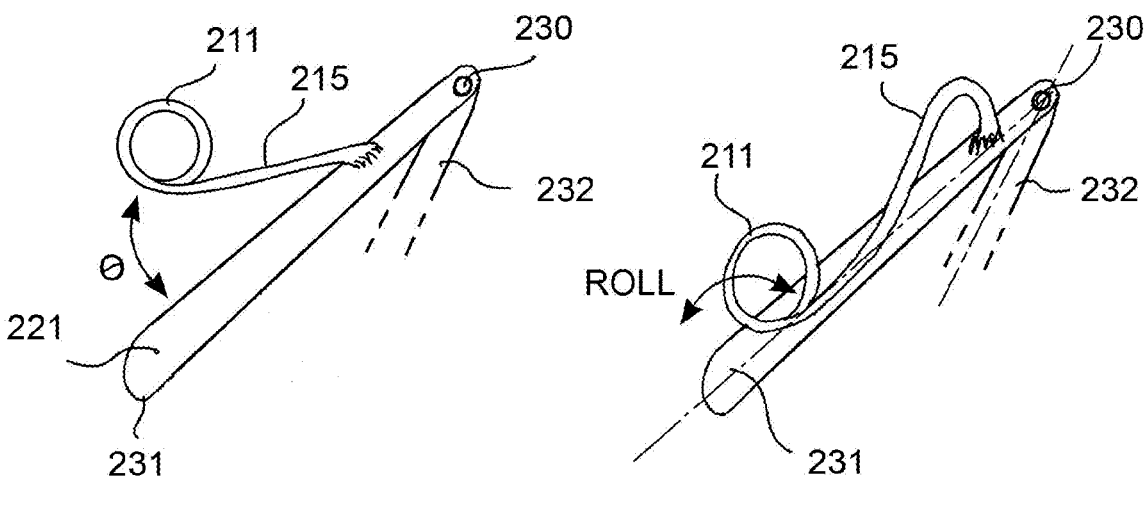

As shown for example in FIGS. 11-A, 11-B and 11-C, the arms 215, 216 of the wearable portion can be laces movable when in opening (arrow Θ) with respect to a respective manipulation surface 221, 222 of the control gripper 220, i.e., away from the longitudinal axis X-X, i.e., away from the respective rigid part 231, 232 of the control gripper 220, and are also movable in roll rotation ROLL around the longitudinal axis X-X or around the respective rigid part of the control gripper.

Figure 12:
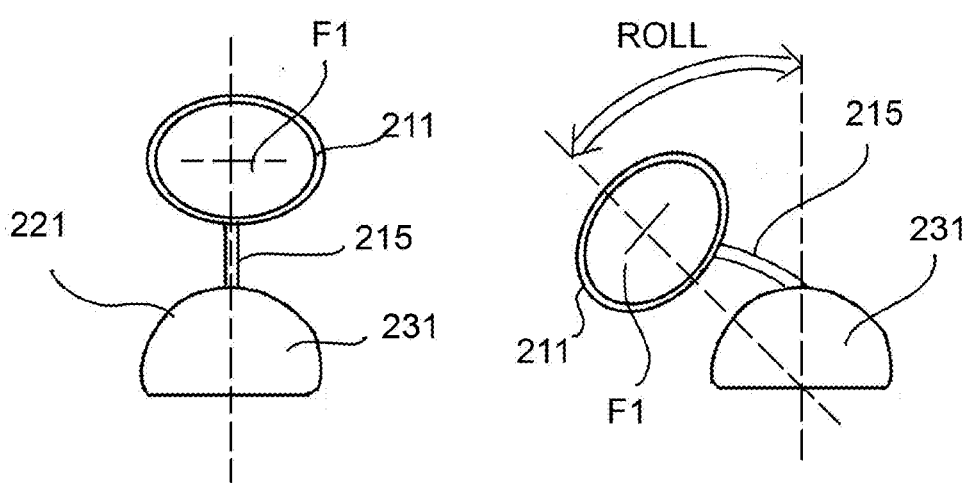
FIGS. 12A and 12B diagrammatically show some possible degrees of freedom of a wearable portion of a master device.

As shown for example in FIGS. 12-A and 12-B, the wearable elements 211, 212 can be rings tightly fitted onto the fingers F1, F2 of the surgeon who is thus able to move the wearable element in roll rotation ROLL with respect to the respective manipulation surface 221, 222 of the operative portion 220.

Figure 13:
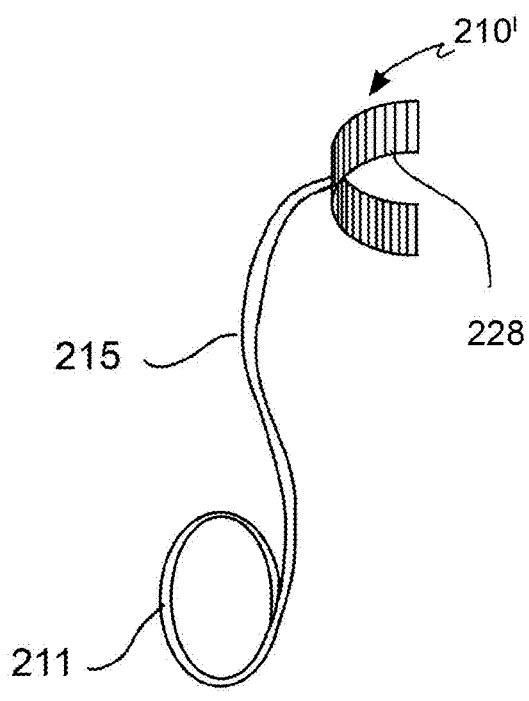
FIG. 13A is an axonometric view of a wearable portion of a master device, according to an embodiment.
FIG. 13B shows in axonometric view a wearable portion of a master device, according to an embodiment.
FIG. 13C shows in axonometric view a master device comprising the wearable portion of FIG. 13A.
Figure 13:
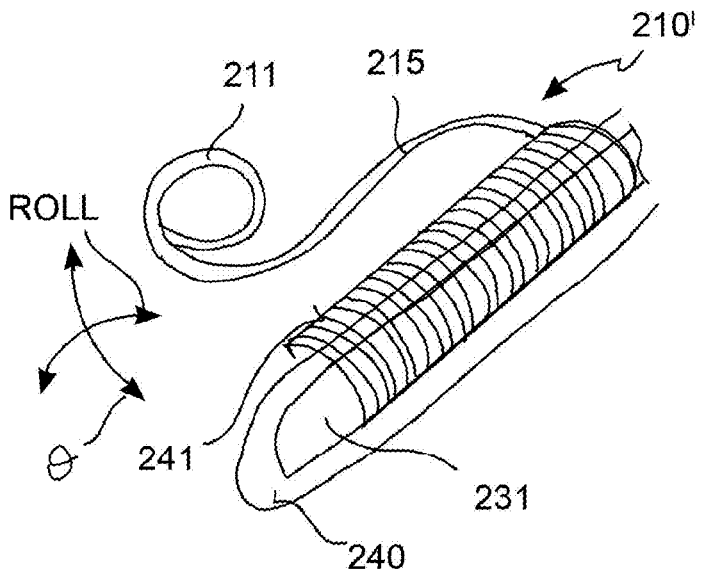
Figure 13:
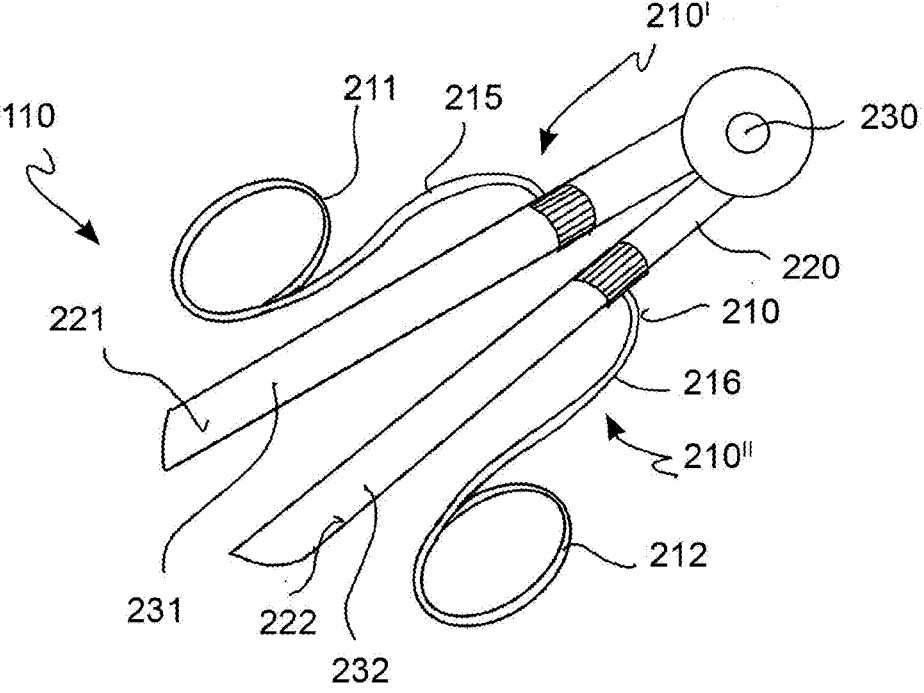

As shown for example in FIGS. 13-A, 13-B and 13-C, the wearable portion 210 can comprise two separate wearable half-portions 210', 210" (a right wearable half-portion 210' and a left wearable half-portion 210", for example), each separate wearable half-portion being connected (e.g., secured) to a respective rigid part 231, 232 of the operative portion 220 by providing a securing clip 218. In accordance with an embodiment, the securing clip 218 of each separate wearable half-portion 210', 210" also forms the respective manipulation surface 221, 222, acting as said sterile accessory 241, 242.

Figure 14:
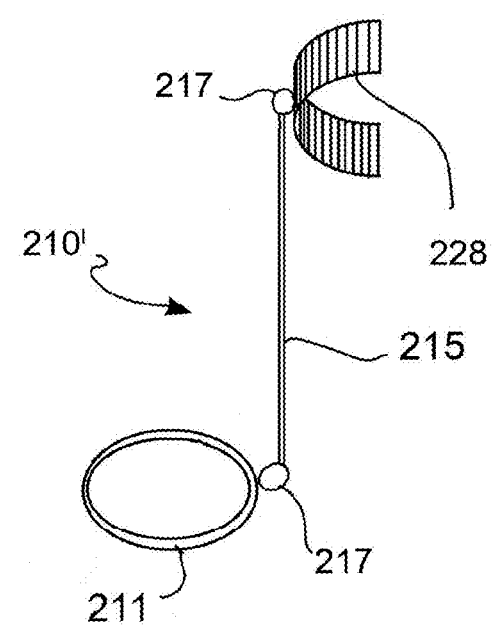
FIG. 14 shows in axonometric view a wearable portion, according to an embodiment.

As shown for example in FIG. 14, a wearable half-portion 210', 210" can comprise an arm 215, 215 and two joints 217 (e.g., hinges) and a securing clip 218 for securing to the operative portion 220. Moreover, the manipulation surface 221 can be provided on the securing clip 218.

Figure 15:
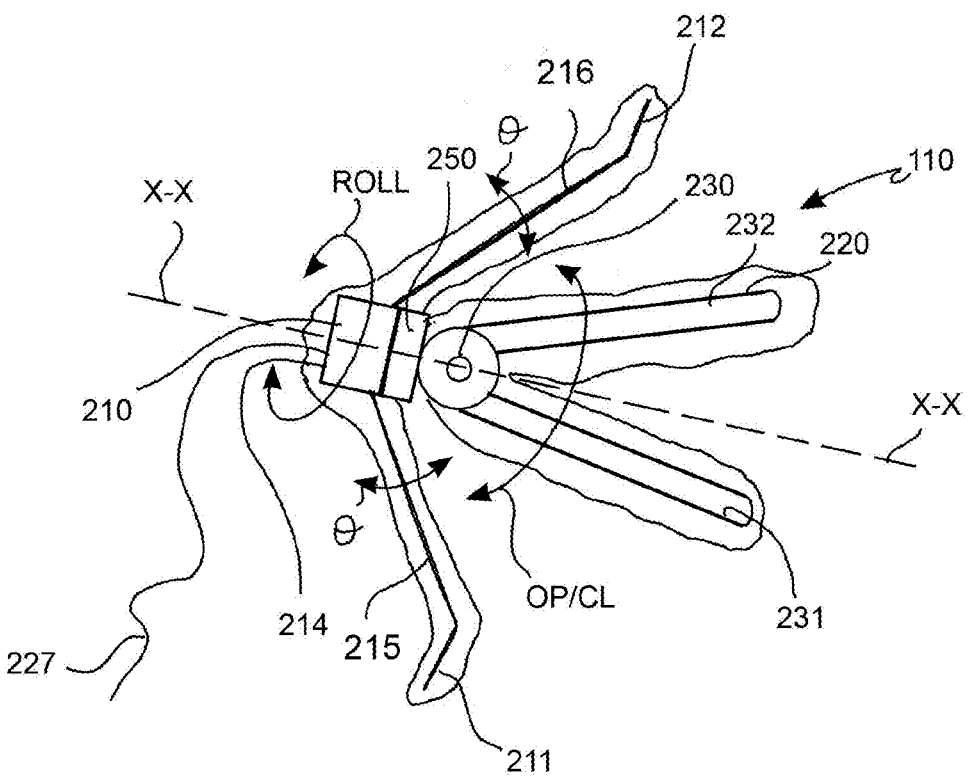
FIG. 15 shows in axonometric view a master device, according to an embodiment.

As shown for example in FIG. 15, the pivotable joint 250 of roll ROLL can be an internal degree of freedom of the wearable portion 210 and in particular of the hollow body 214 of the wearable portion, so that the wearable elements 211, 212 rotate in simultaneous coordination around the longitudinal axis X-X.

Figure 16:
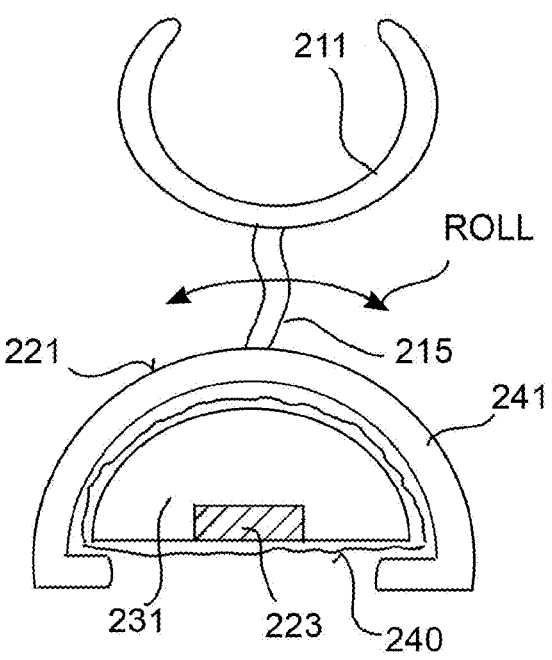
FIG. 16A shows in diagrammatic section a portion of a master controller device, according to an embodiment.
FIG. 16B shows in axonometry the portion of a master controller device of FIG. 16A.
Figure 16:
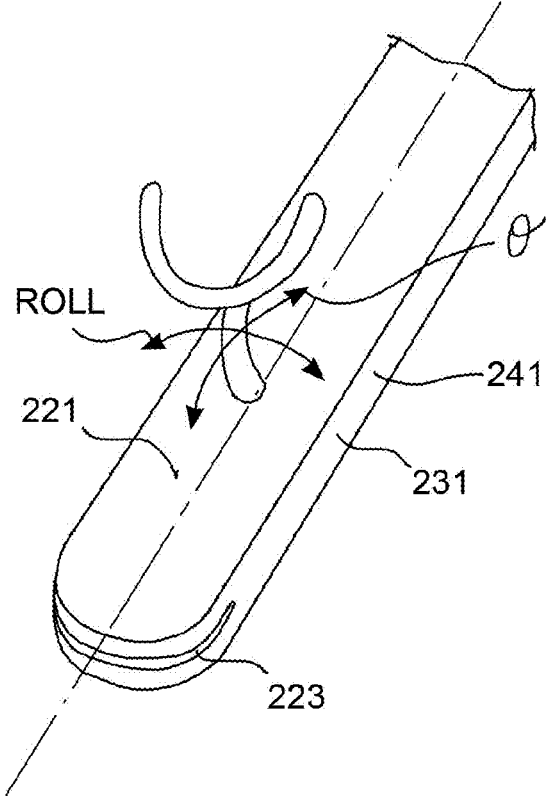

As shown for example in FIGS. 16-A and 16-B, a sterile accessory 241 can be provided, comprising an arm 215 and a wearable element 211 which is coupled to a sensed rigid part 231 of the control gripper 220, allowing the reorientation and repositioning of the wearable element with respect to the manipulation surface 221 as well as with respect to the sensor 223, i.e., with respect to the rigid part 231 of the control gripper, by virtue of the arm 215.

Figure 17:
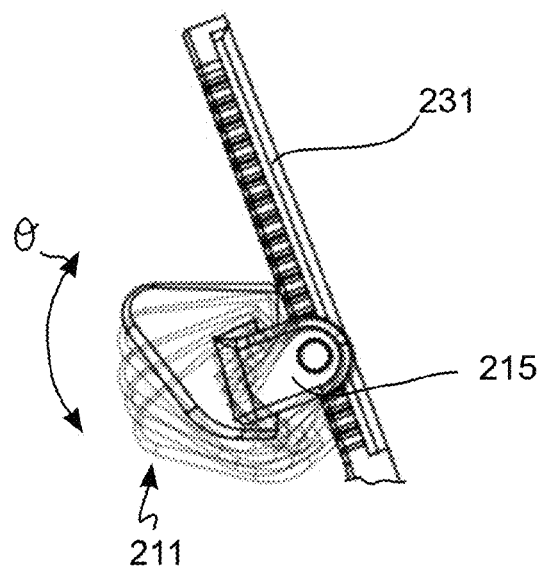
FIG. 17 shows a wearable element of a master controller device, according to an embodiment.

As shown for example in FIG. 17, there can be provided a rotational joint (hinge) associated with the arm 215, which allows reorienting the wearable element 211 with respect to the respective rigid part 231 thereof of the control gripper.

Figure 18:
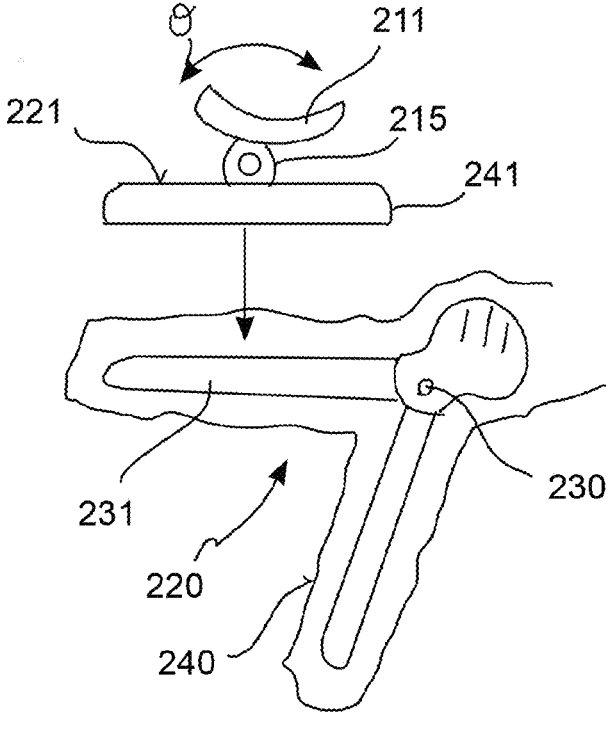
FIG. 18 diagrammatically shows the mounting of a wearable half-portion to the control gripper, according to an embodiment.

As shown for example in FIG. 18, the arm 215 can be made in the form of a joint, for example a ball joint, interposed between a sterile accessory 241 and the respective wearable element 211.

With reference to the embodiments described above, further examples and details of embodiments will be given below.

In accordance with an embodiment, the pair of wearable elements 211, 212 consists of an extended and elongated part 215, 216 or arm 215, 216 or connection element 215, 216 which couples or is constrained to said operative part 220. In accordance with an embodiment, such extended and elongated portions 215, 216 are flexible or elastic such as to follow relative movement between the fingers, the wearable part 210, and the control gripper 220.

In accordance with an embodiment, the wearable elements 211 212 are each connected or referred to one of the two rods 231, 232 or rigid parts 231, 232 of the control gripper 220 and such as to receive two opposite fingers F1, F2 for the movement, manipulation and opening/closing OP/CL of the control gripper 220.

In accordance with an embodiment, the wearable elements 211, 212 are made of an elastic material deformable under the action of even weak external forces, or articulated and flexible laces or articulated mechanical parts/chains. In accordance with a preferred embodiment, the wearable elements 211, 212 have one or more relative degrees of freedom with respect to said rigid parts 231, 232 of the control gripper 220 so as to allow the relative movement and the safe manipulation of the sensed control gripper when gripped.

In accordance with an embodiment, said at least one internal degree of freedom of orientation of the master device 110 comprises a degree of freedom of roll ROLL which allows the rotation of each of the wearable elements 211, 212 around a respective rigid part 231, 232 of the operative portion 220. For example, each rigid part 231, 232 can define an extension direction, which can be coincident with the longitudinal direction X-X when in conditions of closed operative part 220, in which each wearable element 211, 212 is movable at least in roll with respect to the extension axis of the rigid part 231, 232 thereof.

In accordance with one embodiment, the wearable elements 211, 212 are clastic rings with a diameter equal to or smaller than the human finger and on which the fingers are constrained but the elasticity and deformability of which allow the finger to move with respect to the operative part while keeping the ring constrained to the finger.

In accordance with an embodiment, the wearable elements, e.g., rings, of the pair of wearable elements 211, 212 are rigid wearable elements, e.g., rings, with a diameter greater than the human finger and on which the fingers can slide along the surface in relative movements with respect to the operative part, keeping the ring in contact with the finger.

In accordance with an embodiment, the wearable elements, e.g., rings, of the pair of wearable elements 211, 212 are portions of wearable elements, e.g., elastic or rigid rings into which a finger can enter above (i.e., approaching the element from a proximal side) or through (i.e., approaching the element transversely) but also slide along the edges or deform the shape of the partial ring in a relative movement between hand, fingers, portions of wearable elements, e.g., rings, and operative part 220.

In accordance with an embodiment, the wearable elements 211, 212 are concave and rigid flaps mounted on a rotational joint or ball joint with respect to the operative part 220 and in which the fingertip rests and can move relatively.

In accordance with an embodiment, the wearable elements 211, 212 can be directly connected with the rigid rod 231, 232 in a distal area, for example close to a free end of the rigid rod 231, 232.

In accordance with an embodiment, the wearable elements 211, 212 have a connection element 215, 216 or arm extending from the part connected to the rigid part 231, 232 of the control gripper, in which such a connection element is elongated and flexible and/or elastic to receive the relative movement of the wearable part with respect to the sensed part.

In accordance with an embodiment, said elongated element is connected to the respective rigid part 231, 232 in the proximal area and extends unconnected in the distal direction with an elastic, flexible or articulated element towards the distal direction and so as to receive the relative movement of the wearable part with respect to the operative part. For example, in such an embodiment, said elongated element has wearable elements, for example rings, flexible at the free end thereof.

In accordance with an embodiment, there are three degrees of freedom of relative orientation (RPY—roll-pitch-yaw) between said operative part 220 and wearable part 210. In other words, three degrees of freedom of relative orientation are provided between the wearable portion 210 and the operative portion 220. Preferably, each of said three degrees of freedom of orientation allows a relative angular movement equal to or less than 90°, and preferably less than 90°. In accordance with an embodiment, said relative angular movement is less than or equal to 60°. In accordance with an embodiment, there are also one or more degrees of freedom of relative translation between the wearable portion 210 and the operative portion 220. In accordance with an embodiment, such a relative angular movement between operative part 220 and wearable part 210 is limited to an angular excursion equal to or less than 90°, and preferably less than 90°. In accordance with an embodiment, said relative angular movement is less than or equal to 60°.

In accordance with an embodiment, such an angular movement between the control gripper and the wearable part occurs between each wearable ring and the longitudinal extension axis of the respective rigid part 231, 232 or rod.

In accordance with an embodiment, said angular movement between operative part 220 and wearable part occurs with respect to the common axis X-X i.e., the overall roll axis ROLL of the entire master device 110. In accordance with an embodiment, among the wearable elements, e.g., rings, there is only one degree of freedom between the operative part and the wearable part, and it is the degree of freedom of roll ROLL, i.e., of rotation around the longitudinal axis X-X.

In accordance with an embodiment, there are degrees of freedom of both movement and orientation allowed between the wearable part and the sensed one.

In accordance with an embodiment, the sensed portion is covered by a sterile canvas or drape 240 to preserve the sterility of the user's or surgeon's hands. In this scenario, embodiments are possible in which such wearable elements shown above are all connected to a connection element 214, 228 which in turn is integrally connected to the master through the drape. In accordance with an embodiment, there are connection elements which connect on a master whether it is draped or not draped in order to leave the user the freedom to choose the preferred or customized wearable part as well as the operation in a sterile environment close to the operating bed or in a non-sterile environment in a remote area. In accordance with an embodiment, said wearable elements have a connection element 214, 228 with the draped sensed master, i.e., the control gripper 220 and/or with rigid elements 231, 232 or rods of the control gripper.

In accordance with an embodiment, said wearable elements 211, 212 can each be connected to a clip armor 241, 242, or check 241, 242, which is also capable of coupling to the rod 231, 232 through a sterile drape 240 which partly or completely covers said operative part 220. For example, the connection can be press-fit, snap-fit, or geometric interlocking. Preferably, each clip armor 241, 242 is connected to one of the two rods or rigid parts 231, 232 of the control gripper.

In accordance with an embodiment, the wearable elements 211, 212 are attachable and detachable from the control gripper both when draped and when not draped.

In an embodiment, said wearable elements are part of a single piece.

In accordance with a general embodiment, a robotic system for medical and/or surgical teleoperation 100 comprises at least one master controller device 110 according to any of the previously described embodiments, and at least one slave surgical instrument 170 operable under the control of the at least one master controller device 110.

The at least one slave surgical instrument 170 can comprise a slave surgical instrument as described in any of the previously described embodiments.

Preferably, the system 100 is for use in teleoperated robotic microsurgery.

By virtue of the features described above, provided either separately or in combination, where applicable, it is possible to respond to the needs mentioned above, and to obtain the listed advantages, in particular:

the risk of inadvertent fall of the master device with the control gripper thereof is avoided while allowing a variety of reorientation and/or repositioning movements of the rigid parts of the control gripper between the surgeon's fingers;

a degree of freedom is provided inside the master device, and preferably inside the wearable portion of the master device, without the activation of such a degree of freedom resulting in the transmission of any command to the slave device, favoring an ergonomic and firm grip by the surgeon, making the device suitable for long and laborious teleoperation sessions;

preferably, the degree of freedom inside the master device can be achieved by a rotational joint between a wearable element and the respective rigid part of the sensed control gripper, or by one or more elastically flexible parts, or by a coaxial rotational joint provided with rolling members;

preferably, a connection arm is provided between each ring and the respective rigid part of the control gripper, said arm being for example an articulated and/or elastically flexible and/or yielding arm, similar to a lace;

the presence of a possible sterile drape covering the sensed portion of the master device does not inhibit the use of said degree of freedom of the master device;

in particular, an arm can be provided between each wearable element and a respective sterile cheek thereof couplable to the control gripper through the body of the sterile drape;

while holding it in hand, the operative part can be manipulated and rotated between the fingers while the wearable part ensures grip and movement by means of a constraint with the user's fingers/hand ("fall protection safety").

It is well understood that the combinations of features of the appended claims form an integral part of the present description.

Those skilled in the art may make several modifications and adaptations to the above-described embodiments and may replace elements with functionally equivalent elements without, however, departing from the scope of the appended claims.

| LIST OF REFERENCE SIGNS | |
| --- | --- |
| 100 | Robotic system for medical and/or surgical teleoperation |
| 110 | Master controller device, or master device |
| 120 | Vision system |
| 130 | Display of the operative console |
| 140 | Operative console with tracking device |
| 150 | Operator, or user, or surgeon |
| 160 | Robotic manipulator |
| 170 | Slave device, or slave surgical instrument |
| 210 | Wearable portion of the master device |
| 211 | First wearable element or ring |
| 212 | Second wearable element or ring |
| 213 | Cavity |
| 214 | Securing body, or fixed body |
| 214a | First half-body |
| 214b | Second half-body |
| 215 | First arm |
| 216 | Second arm |
| 217 | Rotational joint of the arm |
| 218 | Movable portion |
| 219 | Interlocking means |
| 220 | Operative portion, or control gripper, or sensed portion, device |
| 221 | First manipulation surface |
| 222 | Second manipulation surface |
| 223 | First sensor or marker |
| 224 | Second sensor or marker |
| 227 | Cable connection |
| 228 | Fixing portion |
| 230 | Joint between the rigid parts of the control gripper |
| 231 | First rigid part of the control gripper |
| 232 | Second rigid part of the control gripper |
| 240 | Sterile drape |
| 241 | First sterile armor, or sterile cheek |
| 242 | Second sterile armor, or sterile cheek |
| 250 | Pivotable joint, such as around the gripper |
| X-X | Longitudinal common axis |

-continued

LIST OF REFERENCE SIGNS

| | |
|---|---|
| OPEN/ CLOSE | Slave degree of freedom of opening/closing of the slave device |
| OP/CL | Opening/closing degree of freedom of the control gripper, or motion towards/away from |
| Θ | Degree of freedom of motion towards/away from the wearable element |
| ROLL | Degree of freedom of roll around the control gripper |
| F1, F2 | Fingers of the surgeon's hand |

The invention claimed is:

1. A master controller device for a robotic surgical tele-operation system, comprising:

at least one wearable portion comprising a pair of wearable elements for a surgeon's fingers; and a sensed control gripper for controlling at least one slave degree of freedom of a slave surgical instrument associable with the master controller device, said control gripper comprising two rigid parts movable with respect to each other;

wherein the at least one wearable portion comprises at least one arm mounting a respective wearable element of said pair of wearable elements and connecting the respective wearable element to the sensed control gripper; and wherein the at least one arm provides at least one internal degree of freedom for the master controller device, and which allows reorienting and/or repositioning the respective wearable element of said pair of wearable elements with respect to the control gripper and with respect to the other wearable element of said pair of wearable elements.

2. A device according to claim 1, wherein said at least one internal degree of freedom allows reorienting and/or repositioning both wearable elements of said pair of wearable elements with respect to the control gripper.

3. A device according to claim 1, wherein said at least one internal degree of freedom allows reorienting and/or repositioning each wearable element of the pair of wearable elements individually, without activation of said at least one internal degree of freedom causing transmission of any command to slave surgical instrument.

4. A device according to claim 1, wherein the at least one internal degree of freedom comprises a degree of freedom of translation of at least one wearable element of the pair of wearable elements with respect to the control gripper.

5. A device according to claim 1, wherein said at least one internal degree of freedom comprises a degree of freedom of rotation of the wearable elements around the control gripper.

6. A device according to claim 1, wherein said at least one internal degree of freedom comprises a degree of freedom of rotation of each of the wearable elements around a respective rigid part of the control gripper, individually.

7. A device according to claim 1, wherein said at least one internal degree of freedom comprises a degree of freedom of motion towards/away of at least one wearable element of said pair of wearable elements from the control gripper.

8. A device according to claim 1, wherein each wearable element is movable towards/away from the respective rigid part of the control gripper, individually.

9. A device according to claim 1, wherein said at least one degree of freedom of orientation, allows a limited angular movement equal to or less than 90°.

10. A device according to claim 1, comprising at least one sterile drape to cover the control gripper and secured thereto by the wearable portion.

11. A device according to claim 1, wherein the wearable portion is formed by two separate wearable half-portions, each wearable half-portion comprising a wearable element and a fixing portion securable to the control gripper, and snap-fittable to a respective rigid part of the control gripper; and wherein the wearable element of each wearable half-portion is movable according to said at least one degree of freedom with respect to the respective fixing portion securable to the control gripper.

12. A device according to claim 11, wherein each of the two wearable half-portions or sterile armors comprises a manipulation surface thereof forming the manipulation interface for the surgeon's fingers wearing the respective wearable elements of the master device.

13. A device according to claim 1, comprising a pair of arms including said at least one arm, each arm mounting a respective wearable element of said pair of wearable elements, said arms achieving said at least one internal degree of freedom which allows reorienting and/or repositioning the wearable element of said pair of wearable elements with respect to each other and at least with respect to the two rigid parts of the control gripper.

14. A device according to claim 13, wherein each arm is an elastically deformable arm, in three directions of space, and is preloaded towards a predeterminable rest configuration with respect to the control gripper.

15. A device according to claim 13, wherein each arm comprises one or more rotational joints and/or a ball joint, allowing reorientation of both wearable elements of said pair of wearable elements independently; and wherein said one or more joints are elastically pre-loaded towards a predeterminable rest configuration.

16. A device according to claim 13, wherein said arms each comprise a rotational joint for movement of the wearable elements towards/away from the control gripper; and wherein the rotational joints of the arms have a mutually substantially parallel axis, and substantially parallel to a definable rotation axis between the rigid parts of the control gripper.

17. A device according to claim 13, wherein each wearable element is made as a rigid annular body extending outwards, away from the control gripper, in a cantilevered manner from the respective arm thereof.

18. A device according to claim 13, wherein each arm extends along a respective rigid part of the control gripper and substantially parallel to the respective rigid part of the control gripper; and wherein each arm is elastically pre-loaded towards an open rest configuration in which the wearable elements are out of contact with the control gripper.

19. A device according to claim 13, wherein each arm is formed by a yielding lace or rope.

20. A device according to claim 1, wherein the control gripper comprises one or more optical sensors or markers to determine at least one of the following: position of the master controller device, orientation of the master controller device, degree of opening/closing of the master controller device;

wherein the control gripper comprises two tracking sensors or optical markers to determine position of the master controller device, orientation of the master controller device, and degree of opening/closing of the master controller device;

wherein the control gripper comprises the two sensors being respectively secured to the two rigid parts of the control gripper; and/or wherein the master controller device is unconstrained to an operative console.

21. A device according to claim 1, wherein said pair of arms achieving said at least one internal degree of freedom which allows reorienting and/or repositioning each wearable element of the pair of wearable elements individually at least with respect to two rigid parts of the control gripper.

\* \* \* \* \*